United States Patent [19]
Wittwer et al.

[11] Patent Number: 6,140,054
[45] Date of Patent: Oct. 31, 2000

[54] MULTIPLEX GENOTYPING USING FLUORESCENT HYBRIDIZATION PROBES

[75] Inventors: Carl T. Wittwer; Philip S. Bernard, both of Salt Lake City, Utah

[73] Assignee: University of Utah Research Foundation, Salt Lake City, Utah

[21] Appl. No.: 09/164,023

[22] Filed: Sep. 30, 1998

[51] Int. Cl.[7] .................................................. C12Q 1/68
[52] U.S. Cl. ......................... 435/6; 435/91.2; 536/23.1; 935/77; 935/78
[58] Field of Search .................... 435/6, 91.2; 536/23.1; 935/77, 78

[56] References Cited

U.S. PATENT DOCUMENTS

| | | | |
|---|---|---|---|
| 5,403,707 | 4/1995 | Atwood et al. | 435/5 |
| 5,475,098 | 12/1995 | Hall et al. | 536/23.7 |
| 5,591,578 | 1/1997 | Meade et al. | 435/6 |
| 5,888,739 | 3/1999 | Pitner et al. | 435/6 |

FOREIGN PATENT DOCUMENTS

| | | | |
|---|---|---|---|
| WO 93/16194 | 8/1993 | WIPO | C12Q 1/68 |
| WO 97/46707 | 12/1997 | WIPO. | |
| WO 97/46712 | 12/1997 | WIPO. | |
| WO 97/46714 | 12/1997 | WIPO. | |

OTHER PUBLICATIONS

Lay et al., "Real–Time Fluorescence Genotyping of Factor V Leiden During Rapid–Cycle PCR", Clinical Chemistry 43, No. 12, pp. 2262–2267, 1997.

Bernard et al., "Integrated Amplification and Detection of the C677T Point Mutation in the Methylenetetrahydrofolate Reductase Gene by Fluorescence Resonance Energy Transfer and Probe Melting Curves", Analytical Biochemistry 255, pp. 101–107, 1998.

Ririe et al., "Product Differentiation by Analysis of DNA Melting Curves During the Polymerase Chain Reaction", Analytical Biochemistry 245, pp. 154–160, 1997.

Wittwer et al., "Continuous Fluorescence Monitoring of Rapid Cycle DNA Amplification", BioTechniques 22, pp. 130–138, Jan., 1997.

Wittwer et al., "The LightCycler™: A Microvolume Multi-sample Fluorimeter with Rapid Temperature Control", Bio-Techniques 22, pp. 176–181, Jan. 1997.

Morrison et al., "Quantification of Low–Copy Transcripts by Continuous SYBR® Green I Monitoring During Amplification", BioTechniques, vol. 24, No. 6, pp. 954–962, 1998.

*Primary Examiner*—Kenneth R. Horlick
*Assistant Examiner*—Janell E. Taylor
*Attorney, Agent, or Firm*—Barnes & Thornburg

[57] ABSTRACT

The present invention is directed to a mutation detection kit and method of analyzing multiple loci of one or more nucleic acid sequences for the presence of mutations or polymorphisms. More particularly, the present invention relates to the use of the polymerase chain reaction (PCR) and fluorescently labeled oligonucleotide hybridization probes to identify mutations and polymorphisms based on melting curve analysis of the hybridization probes.

20 Claims, 23 Drawing Sheets

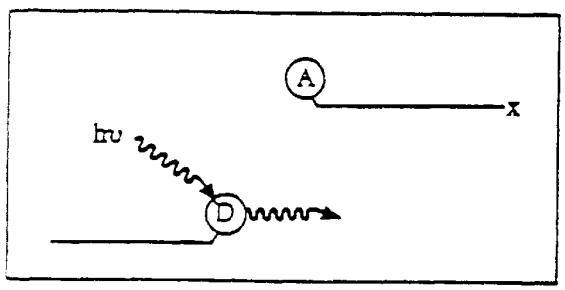
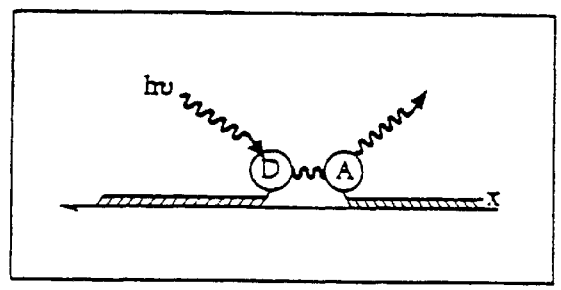
Fig. 3A          Fig. 3B
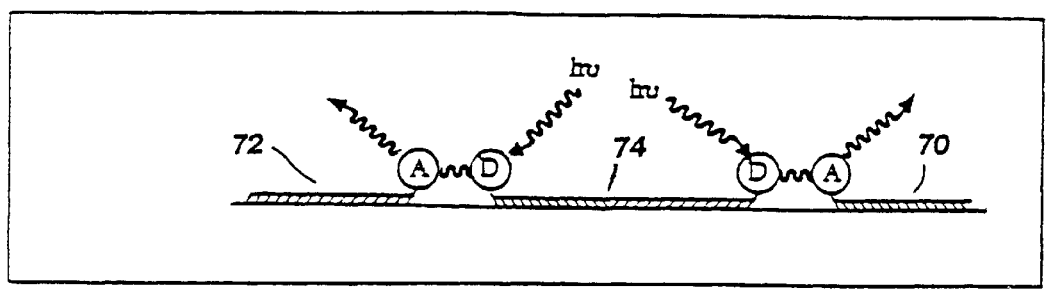
Fig. 3C

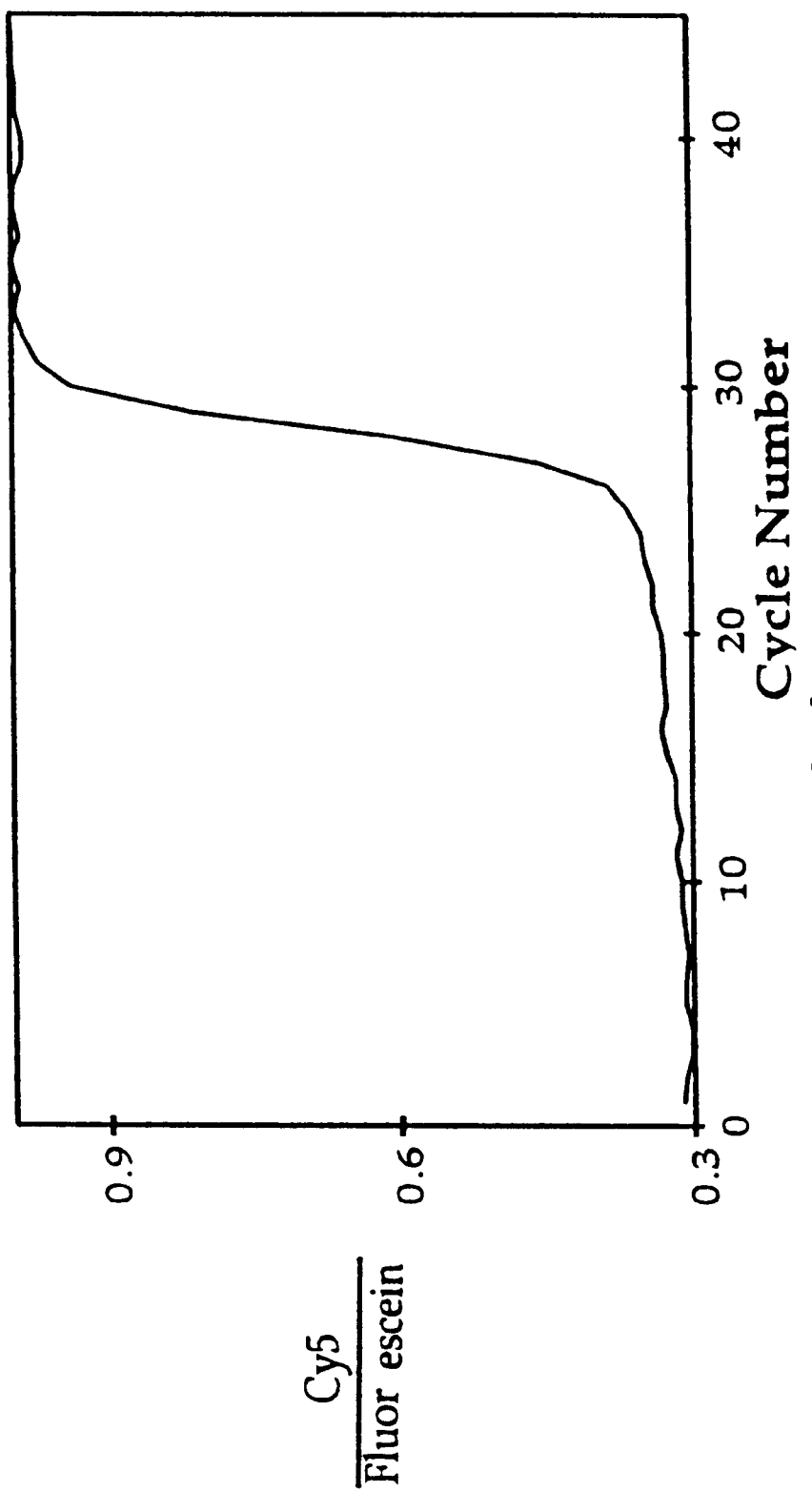

SEQUENCE LISTING

```
<160> NUMBER OF SEQ ID NOS: 22

<210> SEQ ID NO 1
<211> LENGTH: 35
<212> TYPE: DNA
<213> ORGANISM: Homo sapiens

<400> SEQUENCE: 1
caaacagaca ccatggtgca cctgactcct gagga                              35

<210> SEQ ID NO 2
<211> LENGTH: 31
<212> TYPE: DNA
<213> ORGANISM: Homo sapiens

<400> SEQUENCE: 2
gaagtctgcc gttactgccc tgtggggcaa g                                  31

<210> SEQ ID NO 3
<211> LENGTH: 20
<212> TYPE: DNA
<213> ORGANISM: Homo sapiens

<400> SEQUENCE: 3
caacttcatc cacgttcacc                                               20

<210> SEQ ID NO 4
<211> LENGTH: 27
<212> TYPE: DNA
<213> ORGANISM: Homo sapiens

<400> SEQUENCE: 4
gtctgccgtt actgccctgt ggggcaa                                       27

<210> SEQ ID NO 5
<211> LENGTH: 32
<212> TYPE: DNA
<213> ORGANISM: Homo sapiens

<400> SEQUENCE: 5
cctcaaacag acaccatggt gcacctgact cc                                 32

<210> SEQ ID NO 6
<211> LENGTH: 30
<212> TYPE: DNA
<213> ORGANISM: Homo sapiens
```

```
<400> SEQUENCE: 6
gaagtctgcc gttactgccc tgtggggcaa                                    30

<210> SEQ ID NO 7
<211> LENGTH: 46
<212> TYPE: DNA
<213> ORGANISM: Homo sapiens

<400> SEQUENCE: 7
taatctgtaa gagcagatcc ctggacaggc gaggaataca ggtatt                  46

<210> SEQ ID NO 8
<211> LENGTH: 46
<212> TYPE: DNA
<213> ORGANISM: Homo sapiens

<400> SEQUENCE: 8
taatctgtaa gagcagatcc ctggacaggc aaggaataca ggtatt                  46

<210> SEQ ID NO 9
<211> LENGTH: 20
<212> TYPE: DNA
<213> ORGANISM: Homo sapiens

<400> SEQUENCE: 9
taatctgtaa gagcagatcc                                               20

<210> SEQ ID NO 10
<211> LENGTH: 20
<212> TYPE: DNA
<213> ORGANISM: Homo sapiens

<400> SEQUENCE: 10
tgttatcaca ctggtgctaa                                               20

<210> SEQ ID NO 11
<211> LENGTH: 23
<212> TYPE: DNA
<213> ORGANISM: Homo sapiens

<400> SEQUENCE: 11
aatacctgta ttcctcgcct gtc                                           23

<210> SEQ ID NO 12
<211> LENGTH: 23
<212> TYPE: DNA
<213> ORGANISM: Homo sapiens

<400> SEQUENCE: 12
tgaaggagaa ggtgtctgcg gga                                           23

<210> SEQ ID NO 13
<211> LENGTH: 25
<212> TYPE: DNA
<213> ORGANISM: Homo sapiens

<400> SEQUENCE: 13
cctcggctaa atagtagtgc gtcga                                         25

<210> SEQ ID NO 14
<211> LENGTH: 20
<212> TYPE: DNA
<213> ORGANISM: Homo sapiens
```

```
<400> SEQUENCE: 14
aggacggtgc ggtgagagtg                                              20

<210> SEQ ID NO 15
<211> LENGTH: 20
<212> TYPE: DNA
<213> ORGANISM: Homo sapiens

<400> SEQUENCE: 15
tggcaagggt aaacagatcc                                              20

<210> SEQ ID NO 16
<211> LENGTH: 20
<212> TYPE: DNA
<213> ORGANISM: Homo sapiens

<400> SEQUENCE: 16
ctcaggcact cctctcaacc                                              20

<210> SEQ ID NO 17
<211> LENGTH: 20
<212> TYPE: DNA
<213> ORGANISM: Homo sapiens

<400> SEQUENCE: 17
cacatggtta aggcctgttg                                              20

<210> SEQ ID NO 18
<211> LENGTH: 20
<212> TYPE: DNA
<213> ORGANISM: Homo sapiens

<400> SEQUENCE: 18
gatcccaccc tttcagactc                                              20

<210> SEQ ID NO 19
<211> LENGTH: 21
<212> TYPE: DNA
<213> ORGANISM: Homo sapiens

<400> SEQUENCE: 19
agatatacgt accaggtgga g                                            21

<210> SEQ ID NO 20
<211> LENGTH: 35
<212> TYPE: DNA
<213> ORGANISM: Homo sapiens

<400> SEQUENCE: 20
cccaggcctg gatcagcccc tcattgtgat ctggg                             35

<210> SEQ ID NO 21
<211> LENGTH: 27
<212> TYPE: DNA
<213> ORGANISM: Homo sapiens

<400> SEQUENCE: 21
cgtgttctat gatgatgaga gtcgccg                                      27

<210> SEQ ID NO 22
<211> LENGTH: 45
<212> TYPE: DNA
<213> ORGANISM: Homo sapiens
```

-continued

```
<400> SEQUENCE: 22 ggagcccga actccatggg tttccagtag aatttcaagc cagat                    45
```

MULTIPLEX GENOTYPING USING FLUORESCENT HYBRIDIZATION PROBES

US GOVERNMENT RIGHTS

This invention was made with United States Government support under Grant No. GM5 1647, awarded by the National Institute of Health. The United States Government has certain rights in the invention.

FIELD OF THE INVENTION

The present invention is directed to a method of analyzing multiple loci of one or more nucleic acid sequences for the presence of mutations or polymorphisms. More particularly, the present invention relates to the use of the polymerase chain reaction (PCR) and fluorescently labeled oligonucleotide hybridization probes to identify mutations and polymorphisms based on melting curve analysis of the hybridization probes.

BACKGROUND OF THE INVENTION

As databases for polymorphic markers and disease causing mutations continue to grow, there is an increasing need for procedures that can screen nucleic acid sequences for the presence of known polymorphisms and mutations. Optimally, the procedure should be capable of analyzing multiple DNA sites simultaneously (including nucleic acid loci that are physically separated by great distances) for the presence of mutations or polymorphisms.

Current methods for determining the genetic constitution of individuals (genotyping) include oligonucleotide ligation, allele-specific oligonucleotide hybridization, and PCR-restriction fragment length analysis. All these methods require time consuming multiple manual steps. One alternative method of genotyping uses the melting temperature of fluorescent hybridization probes that hybridize to a PCR amplified targeted region of genome/nucleic acid sequence to identify mutations and polymorphisms.

The polymerase chain reaction (PCR) is a technique of synthesizing large quantities of a preselected DNA segment. The technique is fundamental to molecular biology and is the first practical molecular technique for the clinical laboratory. PCR is achieved by separating the DNA into its two complementary strands, binding a primer to each single strand, at the end of the given DNA segment where synthesis will start, and adding a DNA polymerase to synthesize the complementary strand on each single strand having a primer bound thereto. The process is repeated until a sufficient number of copies of the selected DNA segment have been synthesized. During a typical PCR reaction, double stranded DNA is separated into its single strands by raising the temperature of the DNA containing sample to a denaturing temperature where the two DNA strands separate (i.e. the "melting temperature of the DNA") and then the sample is cooled to a lower temperature that allows the specific primers to attach (anneal), and replication to occur (extend). In preferred embodiments a thermostable polymerase is utilized in the polymerase chain reaction. A preferred thermostable DNA polymerase for use in the PCR reaction is the Taq DNA Polymerase and derivatives thereof, including the Stoffel fragment of Taq DNA polymerase and KlenTaqI polymerase (a 5'-exonuclease deficient variant of Taq polymerase—see U.S. Pat. No. 5,436,149).

Thermocycling may be carried out using standard techniques known to those skilled in the art, including the use of rapid cycling PCR. Rapid cycling techniques are made possible by the use of high surface area-to-volume sample containers such as capillary tubes. The use of high surface area-to-volume sample containers allows for a rapid temperature response and temperature homogeneity throughout the biological sample. Improved temperature homogeneity also increases the precision of any analytical technique used to monitor PCR during amplification.

In accordance with the present invention amplification of a nucleic acid sequence is conducted by thermal cycling the nucleic acid sequence in the presence of a thermostable DNA polymerase. The method comprises the steps of placing a biological sample comprising the nucleic acid sequence in a capillary vessel, raising the temperature of the biological sample from a first temperature to a second temperature wherein the second temperature is at least 15° C. higher than the first temperature, holding the biological sample at the second temperature for a predetermined amount of time, lowering the temperature of the biological sample from the second temperature to at least the first temperature and holding the biological sample at a temperature at least as low as the first temperature for a predetermined length of time. The temperature of the biological sample is then raised back to the second temperature, and the biological sample is thermocycled a predetermined number of times. In one embodiment, the method of amplifying a DNA sequence comprises a two temperature cycle wherein the samples are cycled through a denaturation temperature and an annealing temperature for a predetermined number of repetitions. However the PCR reaction can also be conducted using a three temperature cycle wherein the samples are cycled through a denaturation temperature, an annealing temperature and an elongation temperature for a predetermined number of repetitions.

In one embodiment each temperature cycle of the PCR reaction is completed in approximately 60 seconds or less. Rapid cycling times can be achieved using the device and techniques described in U.S. Pat. No. 5,455,175, the disclosure of which is expressly incorporated herein.

In accordance with the present invention PCR amplification of one or more targeted regions of a DNA sample is conducted in the presence of a fluorescently labeled hybridization probes, wherein the probes are synthesized to hybridize to a specific locus present in a target amplified region of the DNA. In a preferred embodiment the hybridization probe comprises two oligonucleotide probes that hybridize to adjacent regions of a DNA sequence wherein each oligonucleotide probe is labeled with a respective member of a fluorescent energy transfer pair. In this embodiment the presence of the target nucleic acid sequence in a biological sample is detected by measuring fluorescent energy transfer between the two labeled oligonucleotides.

Fluorescence resonance energy transfer (FRET) occurs between two fluorophores when they are in physical proximity to one another and the emission spectrum of one fluorophore overlaps the excitation spectrum of the other. The rate of resonance energy transfer is $$(8.785E^{-5}) (t^{-1}) (k^2) (n^{-4}) (q_D) (R^{-6}) (J_{DA}),$$

where:
- t=excited state lifetime of the donor in the absence of the acceptor;
- $k^2$=an orientation factor between the donor and acceptor;
- n=refractive index of the visible light in the intervening medium;
- $q_D$=quantum efficiency of the donor in the absence of the acceptor;

R=distance between the donor and acceptor measured in Angstroms;

$J_{DA}$=the integral of $(F_D)$ $(e_A)$ $(W^4)$ with respect to W at all overlapping wavelengths with:

$F_D$=peak normalized fluorescence spectrum of the donor;

$e_A$=molar absorption coefficient of the acceptor $(M^{-1}cm^{-1})$;

$W^4$=wavelength (nm).

For any given donor and acceptor, a distance where 50% resonance energy transfer occurs can be calculated and is abbreviated $R_0$. Because the rate of resonance energy transfer depends on the 6th power of the distance between donor and acceptor, resonance energy transfer changes rapidly as R varies from $R_0$. At 2 $R_0$, very little resonance energy transfer occurs, and at 0.5 $R_0$, the efficiency of transfer is nearly complete, unless other forms of de-excitation predominate.

Fluorescence resonance energy transfer can be used as a labeling system for detecting specific sequences of DNA. In combination with standard melting curve analysis, single point mutations in a gene can be distinguished from the normal gene. In accordance with one embodiment such a detection system comprises two oligonucleotides that hybridize to adjacent loci on DNA. The oligonucleotides are each labeled, respectively, with one of the fluorophores of a fluorescent resonance energy transfer pair, so that upon hybridization of the two labeled oligonucleotides to their complementary sequences on the targeted DNA, resonant energy is transferred from the donor fluorophore to the acceptor fluorophore. Such an energy transfer event is detectable and is indicative of the presence of the target nucleic acid sequence.

The fluorescently labeled oligonucleotides are designed to hybridize to the same strand of a DNA sequence resulting in the donor and acceptor fluorophores being separated by a distance ranging from about 0 to about 25 nucleotides, more preferably about 0–5 nucleotides, and most preferably about 0–2 nucleotides. A particularly preferred spacing between the donor and acceptor fluorophores is about 1 nucleotide.

When one of the labeled oligonucleotides also functions as a PCR primer ("probe-primer"), then the two fluorescently labeled oligonucleotides hybridize to opposite strands of a DNA sequence. In this embodiment, the donor and acceptor fluorophores are preferably within about 0–15 nucleotides and more preferably within about 4–6 nucleotides.

When both of the fluorescently labeled oligonucleotides are not hybridized to their complementary sequence on the targeted DNA, then the distance between the donor fluorophore and the acceptor fluorophore is too great for resonance energy transfer to occur. Thus the acceptor fluorophore and the donor fluorophore are not in resonance energy transfer relationship and excitation of the donor fluorophore will not produce a detectable increased fluorescence by the acceptor fluorophore.

Acceptable fluorophore pairs for use as fluorescent resonance energy transfer pairs are well know to those skilled in the art and include, but are not limited to, fluorescein/rhodamine, phycoerythrin/Cy7, fluorescein/Cy5 or fluorescein/Cy5.5.

The thermal stability of a DNA duplex relies on duplex length, GC content, and Watson-Crick base pairing. Changes from Watson-Crick pairing destabilize a duplex by varying degrees depending on the length of the mismatched duplex, the particular mismatch, the position of the mismatch, and neighboring base pairs. Accordingly, the percent identity of the hybridization probes to their target complementary sequence directly impacts the temperature at which the hybridization probe will separate (melt) from the complementary strand. The greater the difference between the probe and the target complementary sequence the lower the temperature needed to separate the hybridizing strands. Accordingly, an oligonucleotide probe identical in sequence to the complementary wild type sequence will dissociate from the locus containing a mutation at a lower temperature than it will from the wild type locus. The use of fluorescently labeled hybridization probes enables dynamic monitoring of fluorescence as the temperature of the sample is raised and the melting curve for the hybridization probe is determined. The generated melting curve is then compared to the known melting curve for the normal, mutant or polymorphic sequence to determine the sequence of the target nucleic acid locus.

SUMMARY OF THE INVENTION

The present invention is directed to the simultaneous detection of sequence alterations at two or more loci of an amplified DNA sequence as determined by melting-point analysis of the DNA-probe complexes formed at the respective regions of the PCR amplified DNA. More particularly, PCR primers are selected to amplify a preselected DNA segment containing nucleic acid loci that have been identified as harboring a particular mutation or polymorphism. The hybridization probes are designed to hybridize to the amplified region and span the site containing the mutation or polymorphism. In preferred embodiments the hybridization probes are labeled with a fluorescent label. Preferably, each FRET oligonucleotide pair comprises a pair of oligonucleotide probes including a donor oligonucleotide probe, labeled with a resonance energy transfer donor, and an acceptor oligonucleotide probe, labeled with a resonance energy transfer acceptor. The donor oligonucleotide probe and the acceptor oligonucleotide probe are designed so the two probes hybridize to adjacent regions of the same single strand of DNA and resonance energy is transferred from the donor fluorophore to the acceptor fluorophore when both probes are bound to their respective complement.

BRIEF DESCRIPTION OF THE DRAWINGS

FIGS. 3A and 3B illustrate the mechanism of fluorescence generation for fluorescence monitoring of PCR through the use of a donor and acceptor oligonucleotide probes. FIG. 3C illustrate the mechanism of fluorescence generation for a three oligonucleotide probe system.

DETAILED DESCRIPTION OF THE INVENTION

Figure 1:
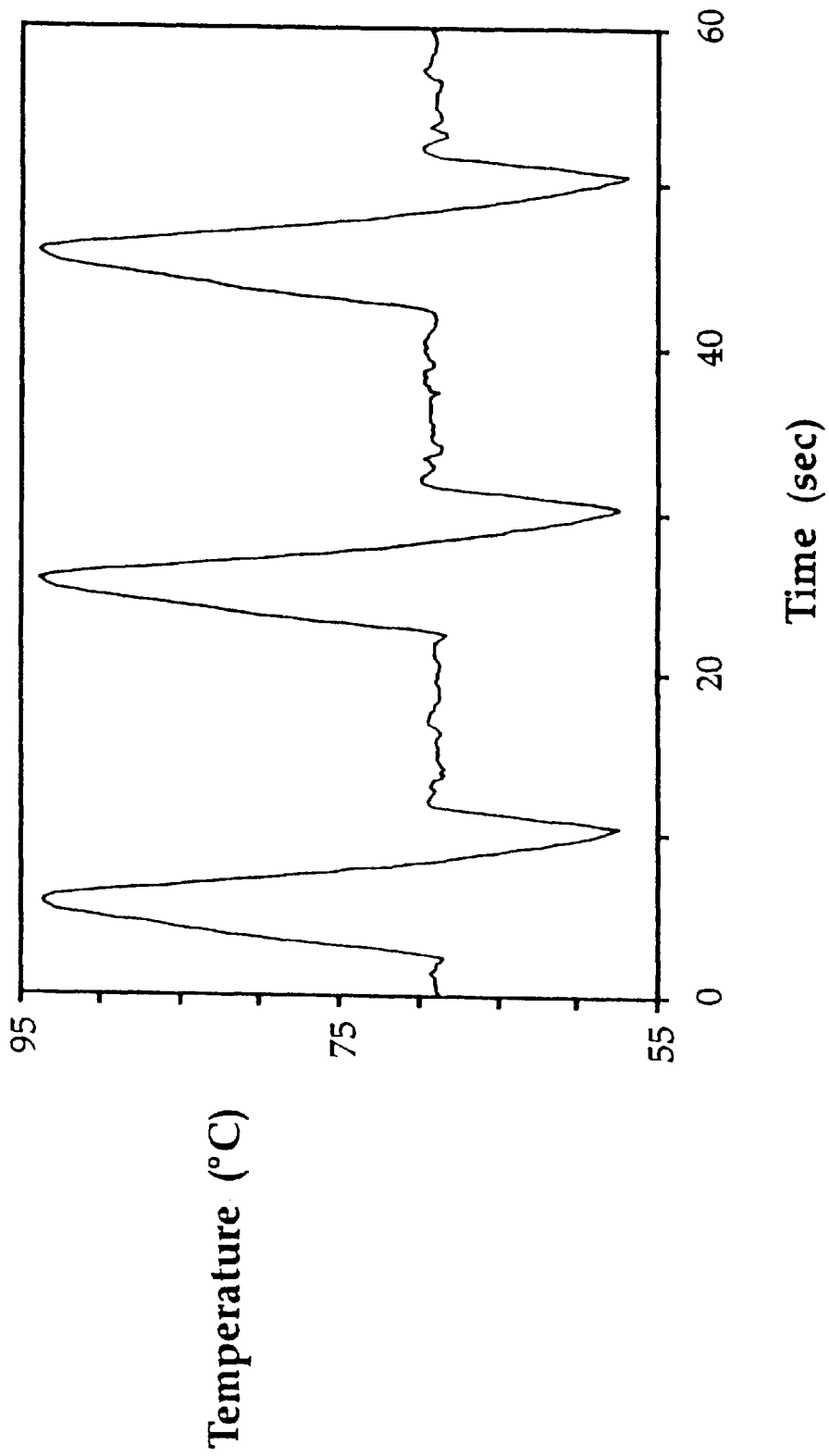
FIG. 1 is a temperature v. time chart exemplary of rapid temperature cycling for PCR.

In describing and claiming the invention, the following terminology will be used in accordance with the definitions set forth below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, "continuous monitoring" and similar terms refer to monitoring multiple times during a cycle of PCR, preferably during temperature transitions, and more preferably obtaining at least one data point in each temperature transition.

As used herein, "cycle-by-cycle" monitoring means monitoring the PCR reaction once each cycle, preferably during the annealing phase of PCR.

As used herein, "fluorescence resonance energy transfer pair" refers to a pair of fluorophores comprising a donor fluorophore and acceptor fluorophore, wherein the donor fluorophore is capable of transferring resonance energy to the acceptor fluorophore. In other words the emission spectrum of the donor fluorophore overlaps the absorption spectrum of the acceptor fluorophore. In preferred fluorescence resonance energy transfer pairs, the absorption spectrum of the donor fluorophore does not substantially overlap the absorption spectrum of the acceptor fluorophore.

As used herein, "fluorescence resonance energy transfer relationship" and similar terms refer to a donor fluorophore and acceptor fluorophore positioned in sufficient proximity and proper orientation to one another to allow the transfer of resonance energy from the donor fluorophore to the acceptor fluorophore.

As used herein, "a donor oligonucleotide probe" refers to an oligonucleotide that is labeled with a donor fluorophore of a fluorescent resonance energy transfer pair.

As used herein, "an acceptor oligonucleotide probe" refers to an oligonucleotide that is labeled with an acceptor fluorophore of a fluorescent resonance energy transfer pair.

As used herein, "FRET oligonucleotide pair" refers to the donor oligonucleotide probe and the acceptor oligonucleotide probe pair that form a fluorescence resonance energy transfer relationship when the donor oligonucleotide probe and the acceptor oligonucleotide probe are both hybridized to their complementary target nucleic acid sequences.

As used herein, "melting temperature of the FRET oligonucleotide pair" and "melting temperature of the set of donor oligonucleotide probe and acceptor oligonucleotide probe", defines the lowest temperature that will disrupt the hybridization of at least one of the pair of oligonucleotide probes (i.e. either the donor or the acceptor oligonucleotide) that are in a resonance energy transfer relationship when both probes are bound to their respective complementary sequence.

As used herein, "effective amount" means an amount sufficient to produce a selected effect. For example, an effective amount of PCR primers is an amount sufficient to amplify a segment of nucleic acid by PCR provided that a DNA polymerase, buffer, template, and other conditions, including temperature conditions, known in the art to be necessary for practicing PCR are also provided.

The present invention is directed to reagents and a method for screening multiple loci of nucleic acid sequences for the presence of mutations or polymorphisms. More particularly, the present invention allows for a rapid procedure, that can be entirely conducted within a single reaction vessel, for detecting mutations and polymorphisms at multiple loci of a genomic DNA sample prepared from an individual organism. The method comprises the steps of combining a biological sample comprising nucleic acid sequences with a pair of oligonucleotide PCR primers, and two or more FRET oligonucleotide pairs, adding a thermostable polymerase, amplifying a selected segment of the nucleic acid sequence by the polymerase chain reaction and illuminating the biological sample and monitoring the fluorescence as a function of temperature.

In one preferred embodiment the PCR reaction is conducted using the rapid cycling techniques described in U.S. Pat. No. 5,455,175. A sample temperature profile during rapid cycle PCR is shown in FIG. 1. Denaturation and annealing appear as temperature "spikes" on these figures, as opposed to the broad plateaus of conventional temperature cycling for PCR. Rapid temperature cycling is contrasted to conventional temperature cycling in FIG. 2, wherein it is shown that 30 cycles of amplification can be completed in 15 minutes and the resulting PCR products contain many fewer side products. Thus, with rapid cycling the required times for amplification are reduced approximately 10-fold, and specificity is improved.

In addition, real time monitoring of a rapid cycling PCR reaction can be conducted through the use of fluorescent dyes and fluorescently labeled probes. Rapid cycle PCR reactions conducted in the presence of fluorescently labeled oligonucleotide probes enables amplification and genotype analysis (by fluorescence monitoring) in thirty minutes or less, more preferably in fifteen minutes or less, and most preferably in ten minutes or less. In one embodiment of the present invention, real time monitoring of a rapid cycling PCR reaction can analyze one or more preselected loci for the presence of a mutation or polymorphism in about 45 minutes. The use of rapid cycling techniques and real time fluorescent monitoring of the PCR reaction have been described in U.S. Pat. No. 5,455,175, issued on Oct. 3, 1995, U.S. patent application Ser. Nos. 08/869,275 and 08/869,276, each filed on Jun. 4, 1997, the disclosures of which are expressly incorporated herein.

Fluorescent probes for use in detecting and monitoring DNA amplifications include double-stranded-DNA-specific dyes and sequence-specific probes. FIGS. 3A and 3B diagrams a hybridization scheme based on resonance energy transfer between fluorophores on two adjacent probes. This method is sequence specific and allows analysis with melting curves. When the 2 labeled probes are hybridized to the same template strand, R can be brought from much greater than $R_0$ to well below $R_0$, increasing resonance energy transfer dramatically.

For example, the fluorescein/rhodamine fluorescence energy transfer pair are commonly used for nucleic acid detection. Unfortunately this fluorescence energy transfer pair has high background fluorescence. Both direct acceptor excitation ($e_A$, ca. 10% $e_{MAX}$) and emission of the donor, at wavelengths are used to detect acceptor emission $p_{DA}$, ca. 20% peak emission), are high. This pair can be used to monitor hybridization if the probe concentration is near to the target concentration and enough time is allowed for complete hybridization. It is not a useful pair of fluorophores for continuous monitoring of PCR because high probe concentrations are required for continuous monitoring of the reaction and the template concentration in PCR is continually changing.

Monitoring product concentration during PCR by hybridization has not been possible in the past because of a lack of an acceptable resonance energy transfer pair. There have been few attempts to use resonance energy transfer for direct "noncompetitive" detection of hybridization. For example, U.S. Pat. No. 5,565,322 states "the observed energy transfer efficiency in terms of re-emission by the acceptor was relatively low." At probe concentrations that are high enough for significant hybridization to occur in seconds, the background fluorescence is too high.

Figure 4:
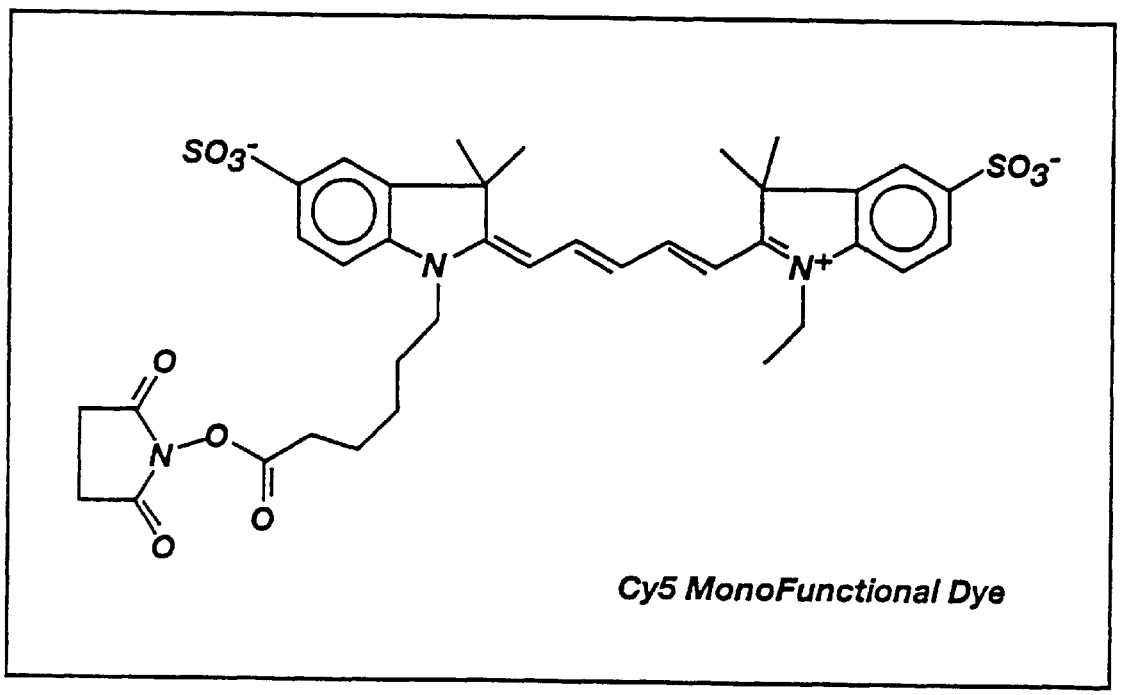
FIG. 4 shows the chemical structure of the monovalent N-hydroxysuccinimide ester of Cy5™.
Figure 5:
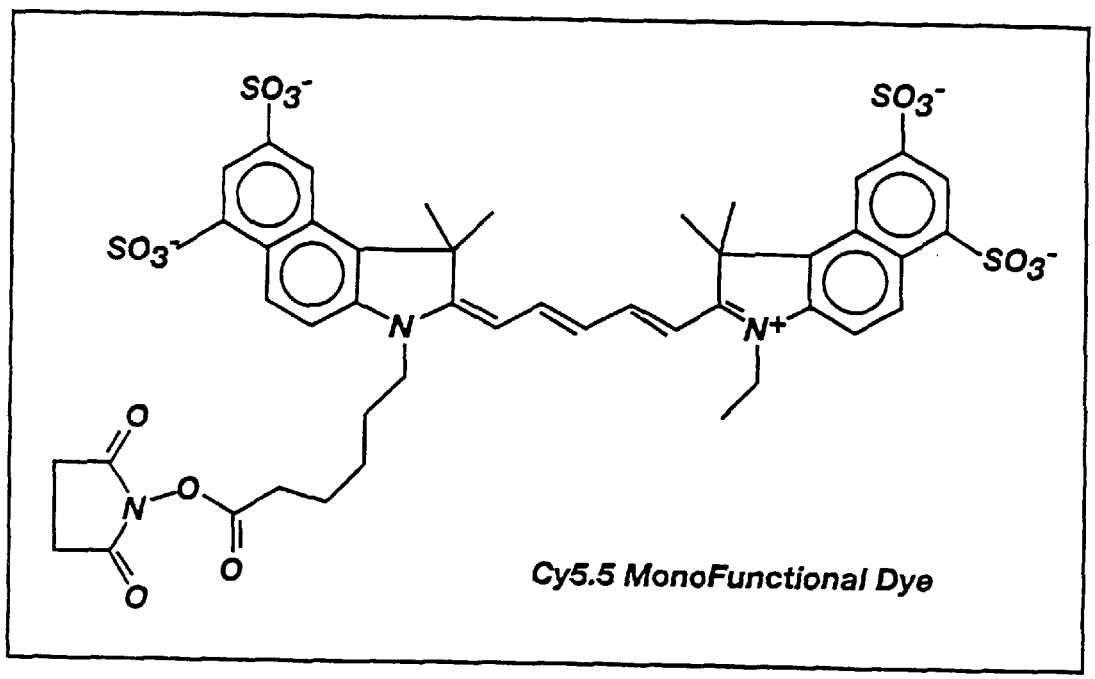
FIG. 5 shows the chemical structure of the monovalent N-hydroxysuccinimide ester of Cy5.5™.
Figure 6:
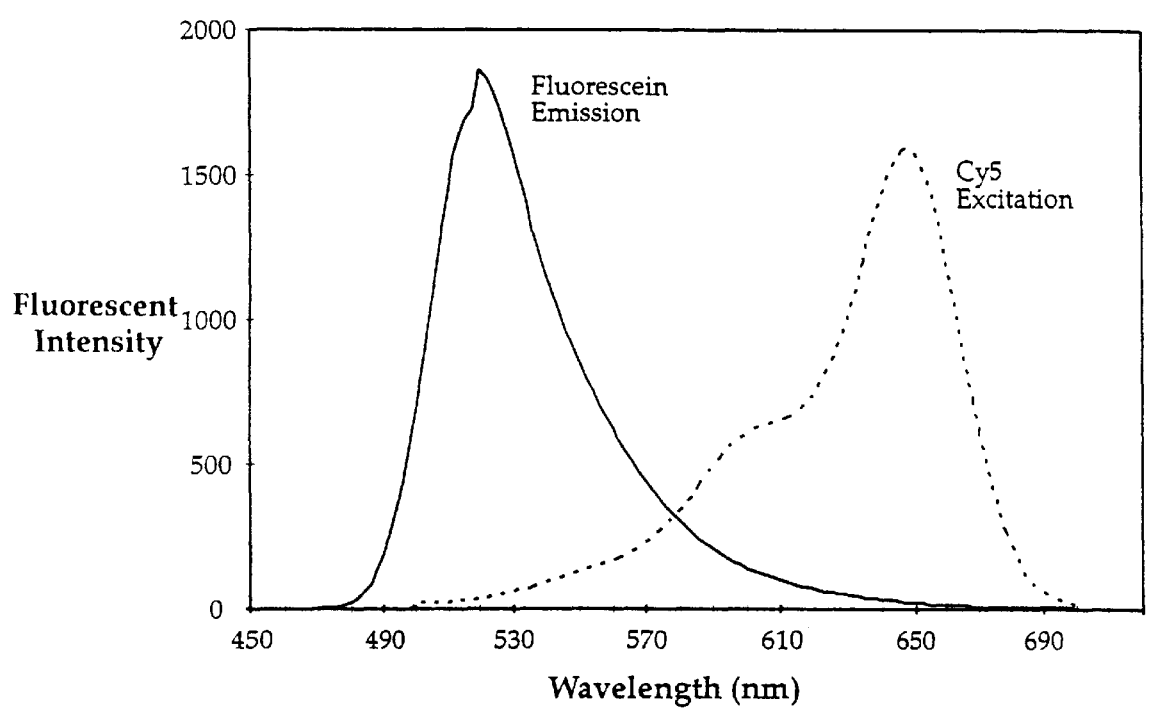
FIG. 6 shows the emission spectrum of fluorescein (solid line) and the excitation spectrum of Cy5 (broken line).

Fluorescein is perhaps the most widely used fluorophore. Its extinction coefficient and quantum efficiency are high and it is extensively used in microscopy, immunoassays, and flow cytometry. As noted above it has been used as the donor in a resonance energy transfer pair with rhodamine. Cy5 is a popular red-emitting fluorophore with a very high extinction coefficient. The structure of the N-hydroxysuccinimide ester of Cy5 is shown in FIG. 4, and the structure of the related dye, Cy5.5, is shown in FIG. 5. These dyes are indodicarbocyanine dyes that are used commonly in flow cytometry and automated fluorescence sequencers and are available from Amersham (Pittsburg, Pa.). Both fluorescein and Cy5 are commercially available as amidites for direct, automated incorporation into oligonucleotides. However, Cy5 is not been commonly used as a resonance energy transfer pair with fluorescein. Intuitively, fluorescein emission and Cy5 absorption do not overlap enough for resonance energy transfer to be considered. The emission spectrum of fluorescein and absorption spectrum of Cy5 attached to oligonucleotides are shown in FIG. 6. When the areas under the curves are normalized, the overlap from the technical spectra is 19%. Cy5.5 excitation is shifted to the red by about 25 nm, further decreasing the overlap with fluorescein emission to about 15%. Working in the red/infrared region of the spectrum is advantageous when choosing optical components for instrumentation. Laser diodes can be used for illumination, photodiode detectors have excellent sensitivity, and most materials have minimal autofluorescence in the pertinent spectral region.

Despite low spectral overlap, it has been discovered that fluorescein and either Cy5 or Cy5.5 make an excellent resonance energy transfer pair for hybridization monitoring during PCR. The unexpectedly good results with the fluorescein/Cy5 pair can at least partly be rationalized. Fluorescein has a long emission "tail" that goes out to 600 nm, 700 nm and beyond that can be used to excite these far red and infrared dyes. The rate of energy transfer is dependent on the overlap integral, but is also effected by the 6th power of the distance between the fluorophores. In addition, the overlap integral, $J_{DA}$ depends not only on spectral overlap, but also on the extinction coefficient of the acceptor (Cy5 has an extinction coefficient of 250,000 $M^{-1}cm^{-1}$ at 650 nm), and on the 4th power of the wavelength. Both of these factors will favor a high $J_{DA}$ for Cy5, even given low spectral overlap. Recently, phycoerythrin and Cy7 were shown to be an effective tandem probe for immunofluorescence, despite low spectral overlap.

If the two fluorescently labeled probes are designed so that the resonance energy transfer dyes are in close proximity, the transfer rate is high. At least with fluorescein/ Cy5, fluorescein/Cy5.5 and like pairs, resonance energy transfer appears to predominate over collisional quenching and other forms of energy loss when the fluorophores are close together, as in the above example where the fluorophores are attached to adjacent probes with no intervening bases.

Fluorescence resonance energy transfer can be used to monitor nucleic acid hybridization even when the interacting dyes have low spectral overlap. The use of fluorescein with Cy5, Cy5.5 and other red or infrared emitting dyes as resonance energy transfer pairs for monitoring hybridization has not been previously recognized.

A device suitable for conducting fluorescent monitored PCR reactions has been describe in U.S. patent application Ser. No. 08/869,275, the disclosure of which is expressly incorporated herein. The device comprises a chamber, a heater and a fan mounted in said device and in air flow communication with the chamber, and a carousel for holding a plurality of sample vessels. The sample vessels used in conjunction with this device comprise an optically transparent material and walls defining a volume having at least first and second dimensions wherein the first dimension is less than the second dimension and wherein the ratio of volume to external surface area of the vessel is less than 1 mm. The carousel is rotatably mounted in the chamber. The device further comprises a light emitting source mounted in said chamber and positioned to illuminate at least one of the sample vessels and a light detector mounted in said chamber and positioned to measure fluorescence from at least one of the sample vessels. In a preferred embodiment the light emitting source and the light detector are mounted in the chamber in a position to illuminate the sample, and detect fluorescence from the sample, along an axis substantially parallel to a wall along the second dimension of the vessel. Furthermore, the device can be equipped with a stepper motor for rotating the carousel to position the respective capillary tubes held by said carousel for illumination and fluorescence detection.

Figure 7:
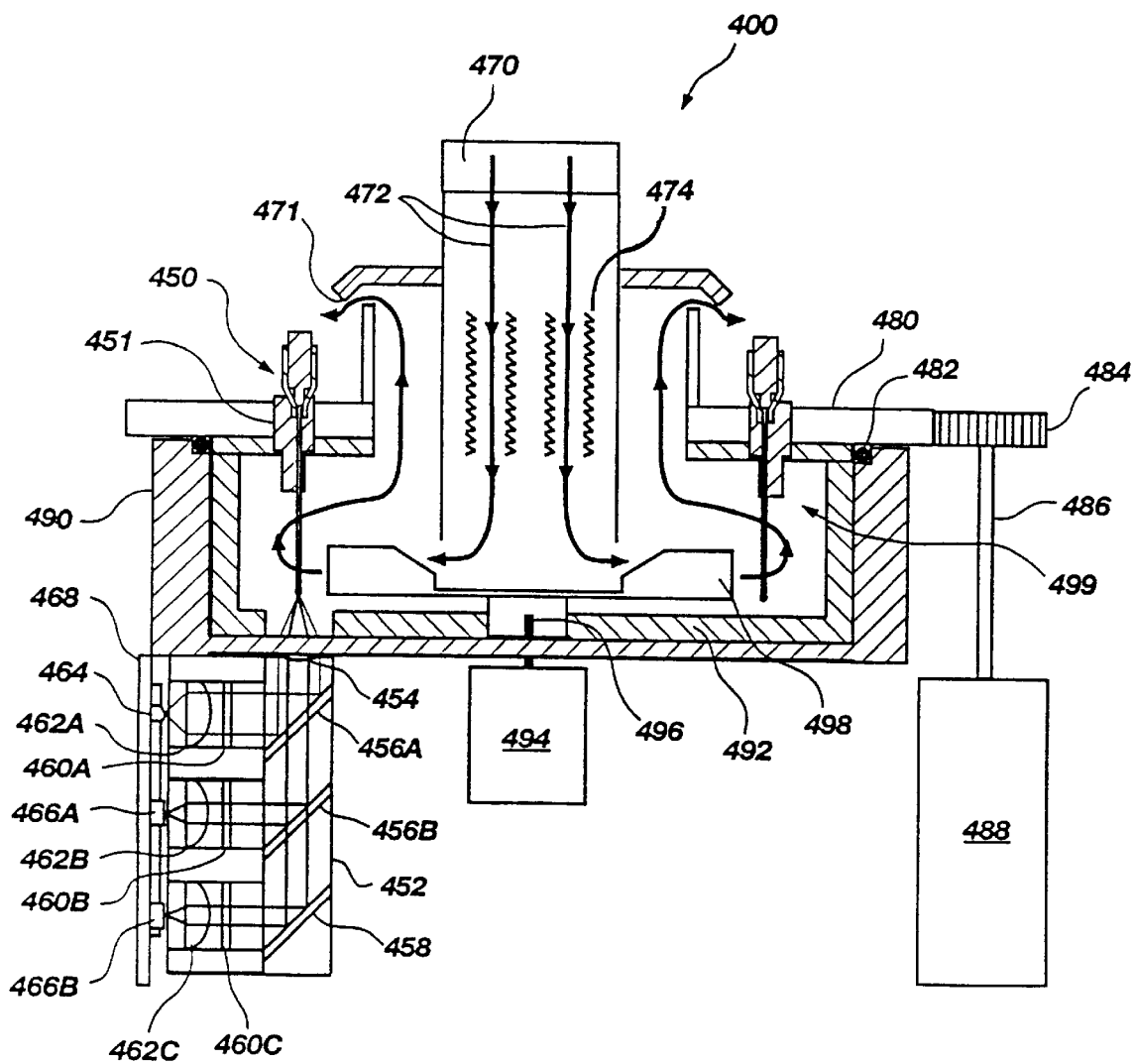
FIG. 7 is a schematic representation of one embodiment of a rapid temperature cycler device with fluorescence detection at the tip of the sample containers.

FIG. 7 provides a schematic representation of one embodiment of a PCR device 400 in accordance with the present invention. The device 400 includes rapid temperature cycling components, sample handling components, and optical components all working together to provide fluorescence detection at the tip of the sample containers (epifluorescence). In the embodiment represented in FIG. 7, air is taken in through an aperture 470 and generally follows the flow path indicated by the lines 472. The temperature of the air, and thus the temperature of the plastic/glass sample container 450, is preferably adjusted using a 400 watt heating cartridge 474 which is preferably one available from Reheat, Inc. The heating cartridge 474 is positioned within a central duct. A fan 498 is provided to move the air in the indicated path 472. The fan is driven via a shaft 496 and a motor 494. The motor 494 is preferably a DC rare earth brush motor which is preferably available from Escap AG. and having a maximum rpm of 15,000.

When heating the plastic/glass sample tubes 450, the heating cartridge is proportionally controlled and the fan is run at a relatively low speed (12 volts, 0.5 amp) to provide temperature homogeneity for all of the plastic/glass sample containers 450. When cooling the plastic/glass sample containers 450, the heating cartridge 474 is disabled and the motor 494 is run at a fast speed (for example with the above-mentioned preferred motor maximum speed is obtained by applying 27 volts, 1.4 amps). The fan 498 forces air into the aperture 470 and out via exhaust ports 471.

In one embodiment twenty-four plastic/glass sample containers 450 (two of which are represented in FIG. 7) are symmetrically arranged around the heating cartridge 474 and the central duct. The plastic/glass sample containers 450 are received by sleeves 451 which (due to their offset structure) allow for precise adjusting of the position of the individual plastic/glass sample containers 450 in a circular carousel 483. The sleeves 451 are preferably fabricated from brass. The off-axis structure of the sleeve 451 allows each sleeve 451 to be aligned so that the tip of the glass/plastic sample container 450 can be precisely adjusted to be at the optical focal point represented in FIG. 7, both laterally and longitudinally.

The carousel 483 is supported on a bearing 482 above a housing 490. The carousel 483 is positioned by a stepper motor 488 provided with a drive gear 484 connected to the motor 488 via a shaft 486. The stepper motor 488 is microstepped (using a controller from New England Affiliated Technologies) to provide over 10,000 steps per revolution of the carousel 483, providing precise positioning of each the plastic/glass sample containers 450. The interior of the housing 490 is provided with an insulative material 492, preferably in accordance with the previously described insulative material. A fluorimeter assembly is supported directly on the mounting board 468 with associated electronics. A collimating lens 454, two dichroic filters 456A and 456B, a mirror 458, interference filters 460A–C, and aspheric focusing lenses 462A–C direct the radiation to and from the sample.

Figure 8:
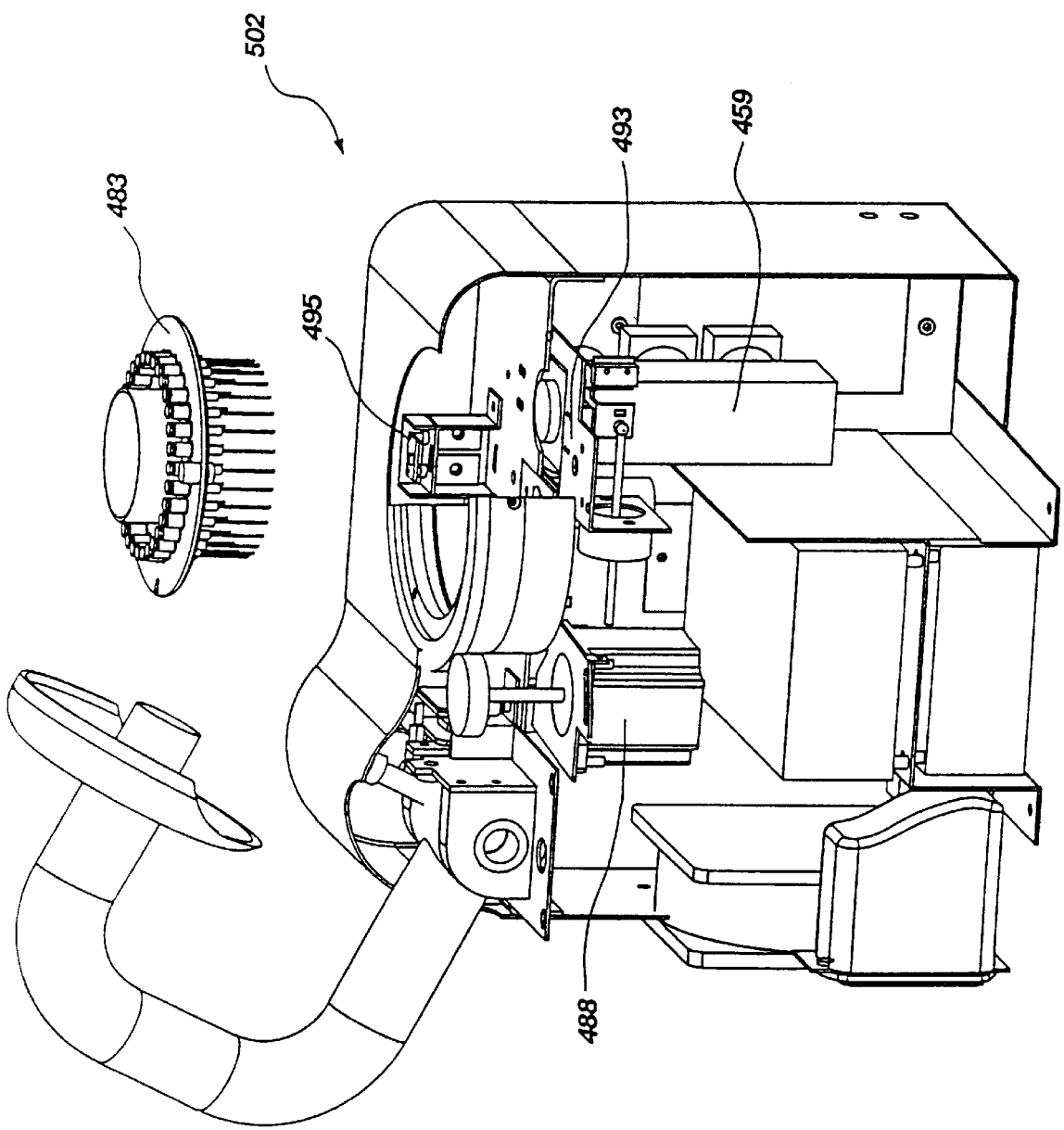
FIG. 8 is a perspective view of the exterior of the rapid temperature cycler device of FIG. 7.

FIG. 8 is a perspective view of the exterior of the embodiment of the present invention including the components illustrated in the schematic representation of FIG. 7. Most advantageously, the fluorimeter is mounted on a slider bearing 493 which is moved by a lateral stepper motor 491. As the carousel 481 rotates, the composite plastic/glass sample containers 450 are precisely positioned over the fluorimeter assembly 459 in the direction of the carousel and the position is noted by the apparatus via the hall effect position locator 495 while the lateral stepper motor 491 adjusts the position of the fluorimeter assembly 459 is adjusted in a second dimension, and the position noted.

Figure 9A:
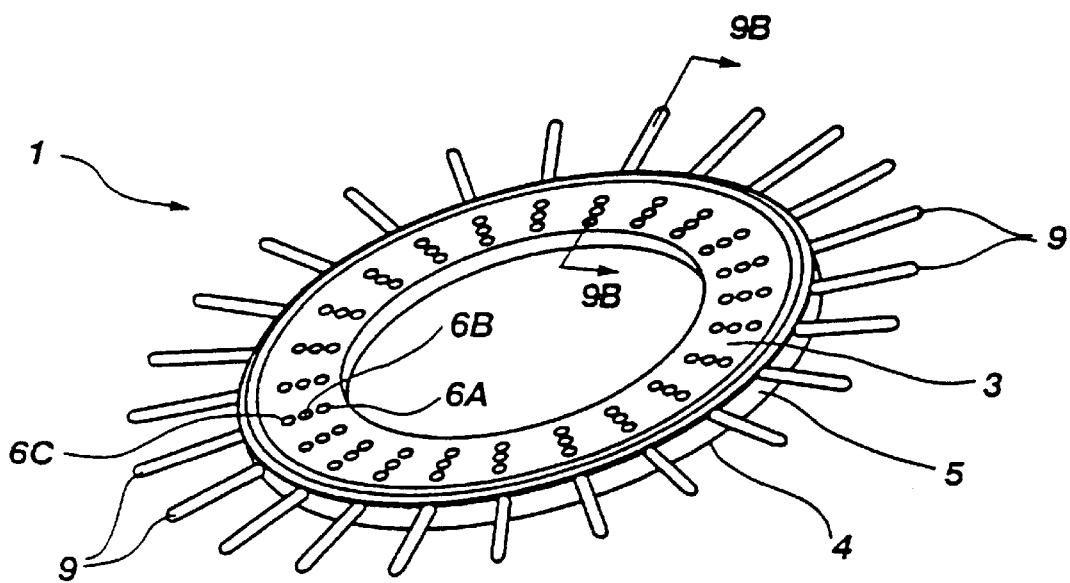
FIGS. 9A and 9B are perspective and cross sectional views, respectively, of a sample handling system for use in a rapid temperature cycler device.
Figure 9B:
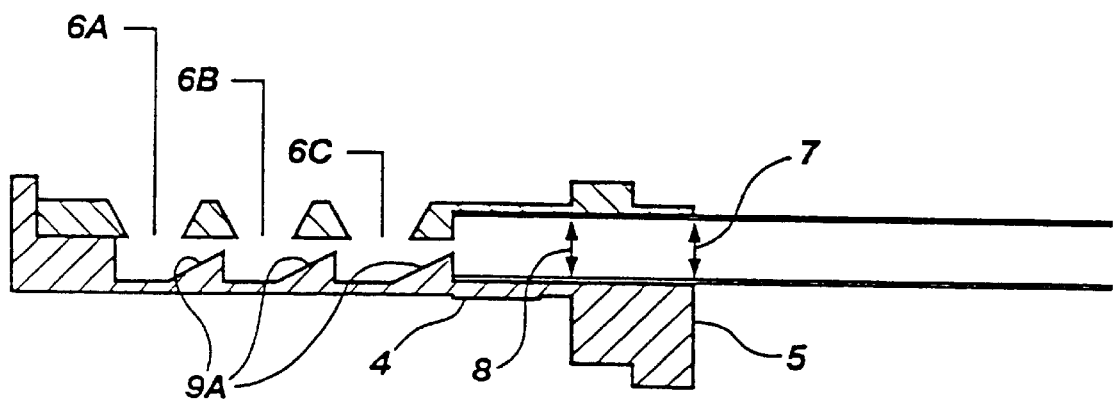

In an alternative embodiment, the multiple sample carousel used is a disc-like structure having a multiplicity of sample receiving ports in the top surface of the disc structure and in fluid communication with corresponding sample vessels attached to the disc. Samples added to the sample receiving ports are transferred to their corresponding sample vessels by rotation of the carousel. Thus in one embodiment the device for conducting fluorescence monitoring PCR reactions comprises a carousel as shown in FIG. 9A and FIG. 9B. Carousel 1 is generally in the form of a disc 2 having a top surface 3, a bottom surface 4 and an outer edge 5 extending therebetween. The disc 2 has a plurality of sets of radially aligned sample receiving ports 6A, 6B, and 6C in the top surface 3, a sample vessel port 7 in outer edge 5 and a sample passageway 8 communicating with the sample receiving ports 6A, 6B, and 6C and the respective sample vessel port 7. Carousel 1 is shown with fixed sample vessels, some of which are indicated at 9. The sample vessel port 7 and sample passageway 8 are formed for receiving and fixing sample vessel 9 to the disc 2. In one embodiment the sample vessel 9 is releasably fixed to the carousel 1 to allow the removal of the sample vessel and its replacement with another sample vessel to allow for multiple use of the carousel 1. In an alternative embodiment the sample vessels 9 are permanently fixed to, or formed as an integral component of, the disc 2. In one embodiment the sample vessel 9 is fixed to the disc 2 by frictional contact between the sample vessel 9 and at least a portion of the sample passageway 8 proximal to said sample vessel port 7. Other conventional means for fixing the sample vessel in communication with the sample vessel can be used. For example, complementary screw threads can be formed on the surface of the sample passageway 8 and on the exterior surface of the sample vessel 9. In addition adhesives or any other fixation means known to those skilled in the art can be used in accordance with the present invention to fix the sample vessel 9 to the disc 2. The top and bottom surfaces of the carousel of the present invention are preferably formed to allow multiple carousels to be stacked one on top of another so that a stack of multiple carousels can be releasably engaged with a motor drive shaft and rotated simultaneously as a unit as shown in FIG. 10.

Figure 10:
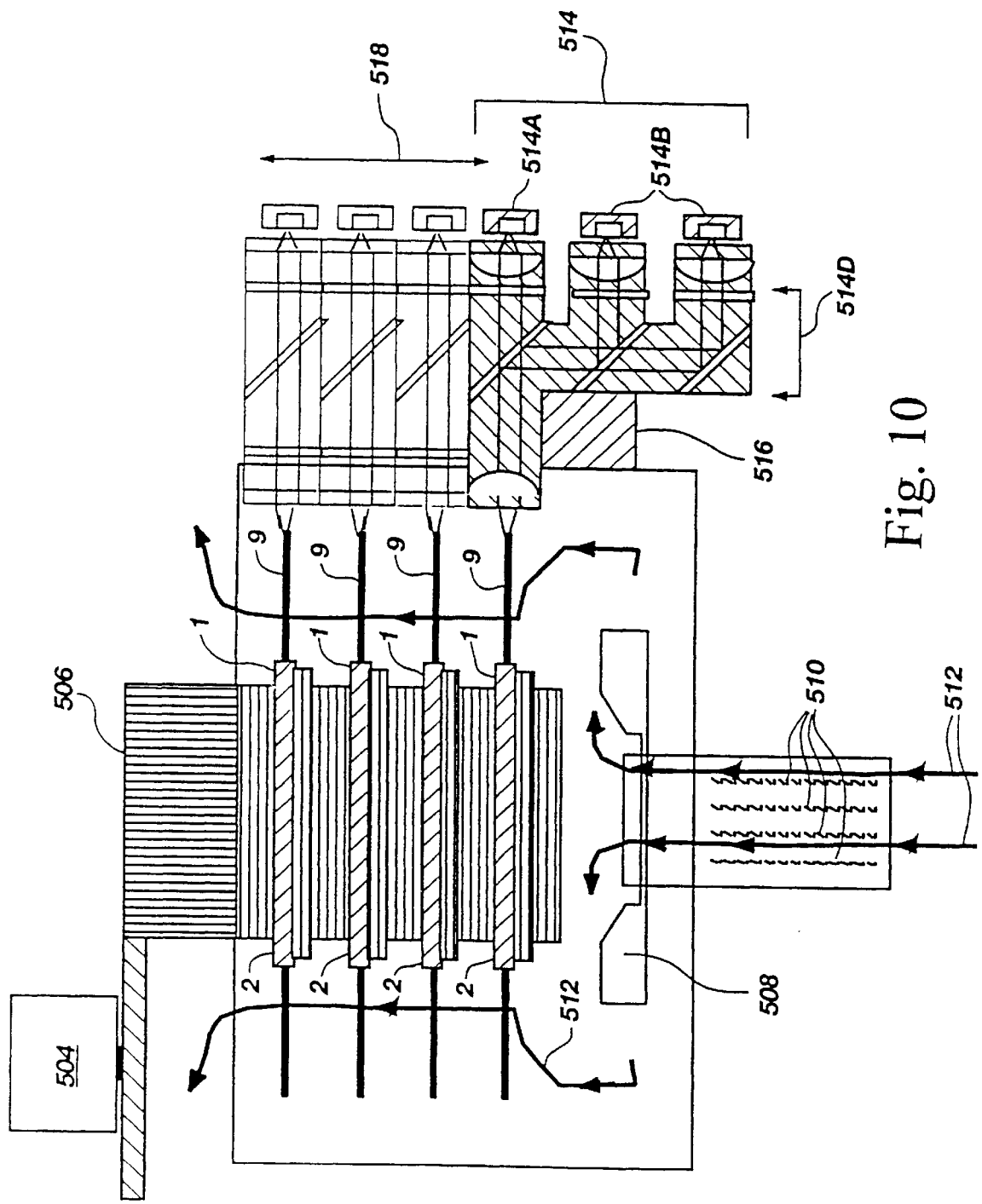
FIG. 10 is a schematic representation of another embodiment of rapid temperature cycler device which accommodates multiple sample handling trays.

The embodiment shown in FIG. 10 includes a stepper motor 504 and a drive shaft 506 which functions to hold and rotate the carousels generally indicated at 1. A chamber fan 508 is used to generate the air flow indicated by the arrows 512. A heating device 510 functions to heat the air which passes by the sample vessels 9. A fluorimeter assembly 514 includes an LED source 514A, photodiodes 514B, focusing lenses 514C, and a filter assembly 514D. A fluorimeter stepper motor 516 functions to move the fluorimeter assembly 514 in the direction of arrow 518.

The PCR primers used to conduct the amplification reactions in accordance with the present invention are selected to hybridize to the respective 3' ends of the complementary strands of the DNA sequence targeted for amplification, so that upon addition of DNA polymerase and the appropriate reaction conditions (known to those skilled in the art), the target segment of the DNA sequence is amplified. The oligonucleotide primers for amplification of the selected mutation locus are preferably about 15 to 30 residues in length. Primers shorter than the preferred range can also be used but may suffer the disadvantage of decreased specificity for the target sequence. Similarly, primers longer than the preferred range could be used, but would be unnecessarily expensive to synthesize. Thus, the limits on the sizes of the PCR primers are only those imposed by functionality.

The FRET oligonucleotide pairs are selected to hybridize to the specific loci suspected of containing a mutation or polymorphism. In a preferred embodiment the 3' terminus of the oligonucleotide probes used in accordance with the present invention are modified, using techniques known to those skilled in the art, to prevent the oligonucleotide probes from serving as a PCR primer. The donor and acceptor oligonucleotide probes constituting the FRET oligonucleotide pair are each preferably about 15–40 nucleotide residues in length, however, these probes can be shorter in length, down to about 10 nucleotide residues. Possible disadvantages of such shorter oligonucleotides include low specificity, low melting temperature, and increased background. Oligonucleotides larger than 40 residues could also be used, but would be unnecessarily expensive to synthesize. Thus, the limits on the size of the probe oligonucleotide are only those imposed by functionality. Each set of oligonucleotide probes comprises a donor oligonucleotide probe and an acceptor oligonucleotide probe wherein the donor and acceptor fluorophores are within about 10 to about 150 angstroms, and more preferably about 22 to about 72 angstroms, of each other when the oligonucleotides are both hybridized to their complimentary target DNA loci.

At least one of the donor and acceptor oligonucleotide probes constituting the FRET oligonucleotide pair should hybridize to the locus containing the mutation. When the mutation involves only a few nucleotides, for example as with point mutations, at least one of the probes should span the locus containing the mutation. Since the lack of base pairing at the termini is known to have less of an effect on melting properties than at internal sites, preferably, the probe spanning the locus containing the mutation/polymorphism is designed such that the position of the mutation/polymorphism corresponds to an internal position of the hybridizing oligonucleotide probe. In synthesizing the FRET oligonucleotide pair either the donor or the acceptor oligonucleotide probe can be selected to span the locus containing the mutation. Alternatively when the mutation involves a large number of nucleotides (i.e. greater than 10 base pairs), such as seen with inversions, translocations, insertions and deletions at least one of the probes should extend into the region of the nucleic acid sequences containing the inserted or deleted sequences (i.e. across the mutation breakpoint), but will not necessarily span the entire region of the nucleic acid sequences containing the inserted or deleted sequences.

In one preferred embodiment the melting temperature of the oligonucleotide probe that hybridize to the mutation locus is designed to have a lower melting temperature than the other oligonucleotide probe of the FRET oligonucleotide pair. Accordingly, the loss of fluorescence from the acceptor fluorophore (as the temperature of the sample is raised) will correspond to the melting temperature of the duplex formed at the locus containing the mutation/polymorphism. In one embodiment, both the donor oligonucleotide probe and the acceptor oligonucleotide probe have higher melting points than the PCR primers used to amplify the selected DNA sequence.

In accordance with the present invention, multiple loci of a target nucleic acid sequence can be analyzed in a single vessel by designing sets of FRET oligonucleotide pairs that hybridize to different genetic loci and have different melting temperatures for each FRET oligonucleotide pair. The sequence of the target loci can then be determined based on the comparison of the melting peaks of the sample with the melting peaks of DNA sequences containing the wild type and mutant loci. Advantageously, the different sets of FRET oligonucleotide pairs can be labelled with the same fluorescent resonance transfer pair, allowing for monitoring at a single emission wavelength. In one embodiment each set of FRET oligonucleotide pairs is labelled with the same fluorescent energy transfer pair, and more particularly the donor oligonucleotide probes are labelled with fluorescein and the acceptor oligonucleotide probes are labelled with Cy5.

Alternatively, the multiple sets of FRET oligonucleotide pairs can be labelled with different fluorescent resonance energy transfer pairs so that the sets of FRET oligonucleotide pairs can be distinguished from one another based on the distinguishable emission spectra. However, the mere reliance on the use of different fluorescent labels is complicated by the limited number of fluorophores available and the overlapping emission spectra of those fluorophores that are available.

In accordance with one embodiment, the method of analyzing multiple loci uses a mixture of FRET oligonucleotide pairs that are labelled with different fluorescent resonance energy transfer pairs that have distinguishable emission spectra as well as FRET oligonucleotide pairs that are labelled with fluorescent resonance energy transfer pairs that have overlapping emission spectra, but are distinguished based on differences in melting temperatures of the respective FRET oligonucleotide pairs. However, the use of multiple sets of fluorescent labels with distinguishable emission spectra complicates the detection and analysis of the emissions from the sample. Accordingly, the design of FRET oligonucleotide pairs having different melting temperatures for each of the FRET oligonucleotide pair is preferred.

In accordance with one embodiment a total of three oligonucleotides are used to detect the presence of mutations or polymorphisms at two separate loci on the same strand of DNA (See FIG. 3C). In accordance with this embodiment the three oligonucleotides hybridize adjacent to one another on the same strand of DNA. The first labeled oligonucleotide 70 hybridizes to the locus containing the first mutation and the third labeled oligonucleotide 72 hybridizes to the locus containing the second mutation. The second labeled oligonucleotide 74 hybridizes to the DNA sequences located between the loci containing the first and second mutations. The second labeled oligonucleotide 74 is labeled at both its 3' and 5' ends with a first member of a fluorescent resonance energy transfer pair. The first and third labeled oligonucleotides are each labeled with the corresponding second member of the fluorescent resonance energy transfer pair so that upon hybridization of all three oligonucleotides to their respective complementary sequences the fluorescent resonance energy transfer pairs are placed in fluorescent resonance energy transfer relationship. In one preferred embodiment the melting temperature of the second labeled oligonucleotide is higher than the melting temperature of the first and third labeled oligonucleotides..

In accordance with one embodiment of the three oligonucleotide probe system, the second labeled oligonucleotide 74 is labeled at both its 3' and 5' ends with a donor fluorophore and the first labeled oligonucleotide 70 and the third labeled oligonucleotide 72 are each labeled at their respective 5' and 3' ends with an acceptor fluorophore (see FIG. 3C). Alternatively the second labeled oligonucleotide can be labeled at both its 3' and 5' ends with an acceptor fluorophore and each of the first and third labeled oligonucleotides can be labeled with a donor fluorophore. Finally, the second labeled oligonucleotide can be labeled at one end with an acceptor fluorophore and the other end labeled with a donor fluorophore and the first and third labeled oligonucleotides are each labeled with the corresponding member of the fluorescent resonance energy transfer pair so that upon hybridization of all three oligonucleotides to their respective complementary sequences the fluorescent resonance energy transfer pairs are placed in fluorescent resonance energy transfer relationship.

In accordance with one embodiment, the fluorescent resonance energy transfer pair located at the 3' end of the first labeled oligonucleotide and the 5' end of the second labeled oligonucleotide is the same as the fluorescent resonance energy transfer pair located at the 5' end of the third labeled oligonucleotide and the 3' end of the second labeled oligonucleotide. In accordance with this embodiment the melting temperature of the first labeled oligonucleotides is different from the melting temperature of the third labeled oligonucleotide. In one preferred embodiment, the donor fluorophore is fluorescein and the acceptor fluorophore is Cy5 or Cy5.5. Alternatively, the fluorescent resonance energy transfer pair located at the 3' end of the first labeled oligonucleotides and the 5' end of the second labeled oligonucleotide can be different from the fluorescent resonance energy transfer pair located at the 5' end of the first labeled oligonucleotides and the 3' end of the second labeled oligonucleotide.

In accordance with one embodiment a method of analyzing a biological sample comprising a nucleic acid sequence for the presence of mutations or polymorphisms at multiple loci of the nucleic acid sequence is conducted by determining the melting temperature of a hybridization probe that is complementary to the locus containing the mutation or polymorphism. The method is conducted in a single reaction vessel and comprises the steps of combining said biological sample with a pair of oligonucleotide PCR primers, a first donor oligonucleotide probe, a first acceptor oligonucleotide probe, a second donor oligonucleotide probe and second acceptor oligonucleotide probe, amplifying the selected segment of the DNA and determining the melting temperature of each set of donor and acceptor oligonucleotide probes. In accordance with this procedure, the pair of oligonucleotide PCR primers are configured for amplifying a selected segment of the nucleic acid sequence. The first and second donor oligonucleotide probes and the first and second acceptor oligonucleotide probes are designed to hybridize to the selected segment so that hybridization of both the first donor oligonucleotide probe and the first acceptor oligonucleotide probe to the selected segment places the first donor oligonucleotide probe and the first acceptor oligonucleotide probe in a resonance energy transfer relationship, and hybridization of both the second donor oligonucleotide probe and the second acceptor oligonucleotide probe to the selected segment places the second donor oligonucleotide probe and the second acceptor oligonucleotide probe in a resonance energy transfer relationship.

To determine the melting curve for each set of donor oligonucleotide probe and acceptor oligonucleotide probes, the biological sample is illuminated with light that is absorbed by the donor fluorophore of the first and second donor oligonucleotide probes and the fluorescence of the sample is monitored as a function of temperature. More particularly, the fluorescence of the first and second acceptor fluorophore is measured as the temperature of the sample is raised until a baseline level of acceptor fluorophore fluorescence is achieved. In one embodiment the temperature dependent fluorescence is monitored after completion of the PCR reaction. In an alternative embodiment the temperature dependent fluorescence is monitored in real time during the PCR reaction.

The method of conducting a PCR amplification reaction while simultaneously determining the fluorescence change as a function of temperature allows for a more rapid genotyping of the target loci. In the past, only endpoint detection was possible because of instrument limitations. However, recently a device and a procedure for conducting real time monitoring of PCR reaction has been described in U.S. Pat. No. 5,455,175, issued on Oct. 3, 1995, and in U.S. patent application Ser. Nos. 08/869,275 and 08/869,276, each filed on Jun. 4, 1997, the disclosures of which are expressly incorporated herein. In general, a high intensity light emitting diode is used for sample illumination, and photodiodes are used for detection. Samples are loaded into glass capillary sample tubes, or alternatively into composite glass/plastic sample tubes in a 96-well format that does not require heat sealing. In performing continuous monitoring, a sample is placed at the intersection of a temperature-controlled air stream and a linear optical path. One side of the capillary is illuminated with a light emitting diode, and the other side is observed with a photodiode. In one embodiment the sample is illuminated, and the emitted sample fluorescence is detected, through the end of the capillary vessel. Air is constantly forced over the sample and the temperature is controlled by a heating element such as a heating coil or an incandescent bulb.

To distinguish the melting point peaks of the two sets of probes, the probes are designed so the melting temperature of each set of probes is different from the melting temperature of the other set of probes. In preferred embodiments the multiple sets of FRET oligonucleotide pairs are each labeled with the same fluorescent resonance energy transfer pair and each FRET oligonucleotide pair has a distinct melting temperature range.

The present invention can be used to detect any known mutation where a hybridization probe can be designed, using standard techniques known to those skilled in the art, to differ in melting temperature when hybridized to mutant vs wild type. The hybridization probes will typically be designed to detect a single base pair mutation (point mutation), however, other mutations, such as insertions, deletions, inversions, tranversions and multiple point mutations in a single locus, can also be detected by using the techniques of the present invention. When hybridization probes are used to detect inversions, tranversions, insertions or deletions, at least one of the donor or acceptor oligonucleotide probes will extend into the region of the nucleic acid sequences containing the inserted or deleted sequences, but will not necessarily span the entire region of the nucleic acid sequences containing the inserted or deleted sequences.

In accordance with one embodiment of the present invention, one probe in each set of FRET oligonucleotide pairs is labeled at its 5' end with a fluorescent energy transfer acceptor selected from the group consisting of Cy5, Cy5.5 and other red or infrared emitting dyes, and the other probe of each set is labeled at its 3' end with fluorescein, a fluorescent energy transfer donor. Since both fluorescent probes used in this method can be synthesized directly from the amidites, a manual synthesis is not required as it is in double labeled probe or primer/probe hydrolysis systems. In one preferred embodiment, at least one of the probes in each set is designed such that the mutation locus corresponds to a complementary sequence located near the center of the probe. Furthermore, the donor and acceptor probes of each set have been modified to prevent them from serving as PCR primers and are designed to hybridize to adjacent regions of the target DNA. Preferably, the donor and acceptor fluorophores are within 0–25 nucleotides, more preferable within 0–5 nucleotides, and most preferable within 0–2 nucleotides upon hybridization of the donor and acceptor probes to their complementary sequences. A particularly preferred spacing is 1 nucleotide. Because background from fluorescein is more troublesome than that from Cy5, the concentration of the Cy5-labeled probe should preferably be 2–5 fold that of the fluorescein-labeled probe.

In accordance with one aspect of the present invention, real time fluorescence monitoring of the PCR reaction is used to acquire product melting curves during the PCR reaction. The temperature cycles of PCR that drive amplification alternately denature the accumulating product and the fluorescently labeled hybridization probes at a high temperature, and anneal the primers and the hybridization probes to the product at a lower temperature. The transition temperatures of the fluorescently labeled hybridization probes depend primarily on GC content and length. If a probe is designed to hybridize internally to the PCR product, the melting temperature of the probe also depends on GC content, length, and degree of complementarity to the target. Plotting fluorescence as a function of temperature as the sample is heated through the dissociation temperature of the product gives a PCR product melting curve. The shape and position of this DNA melting curve is a function of GC/AT ratio, length, and sequence, and can be used to differentiate amplification products separated by less than 2° C. in melting temperature. Thus continuous monitoring of fluorescence during the PCR reaction provides a system for detecting sequence alterations internal to the PCR primers by resonance energy transfer and probe melting curves.

The invention is further directed to a method of co-amplifying two or more separate regions of nucleic acid using at least two sets of PCR primers and at least two sets of FRET oligonucleotide pairs as probes to simultaneously genotype the separate regions by analyzing the melting temperature of the sets of FRET oligonucleotide pairs. In this manner several different genes can be screened simultaneously in a single reaction vessel for the presence of known mutations or polymorphisms.

The method of analyzing a biological sample for the presence of mutations or polymorphisms at multiple loci of nucleic acid sequences can be conducted in a single reaction vessel. In accordance with one embodiment, the method comprising the steps of combining a biological sample with a first and second pair of oligonucleotide PCR primers, a first donor oligonucleotide probe, a first acceptor oligonucleotide probe, a second donor oligonucleotide probe and second acceptor oligonucleotide probe. A thermostable polymerase is then added and the first and second selected segments are amplified by the polymerase chain reaction and the biological sample is illuminated and the fluorescence of the sample is monitored as a function of temperature.

In this embodiment, the first pair of oligonucleotide primers is configured for amplifying a first selected segment of said nucleic acid sequences, and said second pair of oligonucleotide primers is configured for amplifying a second selected segment of said nucleic acid sequences. The first and second selected segments can be located at great distances from one another and can be located on different DNA sequences.

The oligonucleotide probes are designed so the first donor oligonucleotide and first acceptor oligonucleotide probes hybridize to the first selected segment in a manner that places the first donor oligonucleotide probe and the first acceptor oligonucleotide probe in a resonance energy transfer relationship. In addition, the second donor oligonucleotide and second acceptor oligonucleotide probes are designed so the that hybridize of these probes to the second selected segment places the second donor oligonucleotide probe and the second acceptor oligonucleotide probe in a resonance energy transfer relationship. In one embodiment, the first FRET oligonucleotide pair are labeled with the same fluorescence resonance energy transfer pair as the second FRET oligonucleotide pair, but the melting temperature of the first FRET oligonucleotide pair is different than the melting temperature of the second FRET oligonucleotide pair. In one embodiment the donor is fluorescein and the acceptor fluorophore is Cy5 or Cy5.5.

It should also be recognized that although the invention is described with respect to the detection of mutations in genomic DNA, the same principles can be applied to detection of a mutation in cDNA. Preparation of the cDNA requires extra process steps and time, as is well know in the art, thus it is preferred to use genomic DNA because of the advantages of speed and lower cost. However, the use of the present procedures to analyze cDNA can be used to identify defects that are not present in the genomic DNA sequence. For example the present methods can be used on cDNA sequences to identify errors introduced during preparation of the cDNA as well as identifying errors arising from in vivo defects in splicing or other transcriptional or post transcriptional defects. Further, the same technique can be used to detect insertion and deletions in nucleic acid sequences by designing hybridization probes that have altered melting temperature when hybridized to a locus containing the mutation or polymorphism.

The invention is further directed to a kit for genotyping a biological sample for a mutation or polymorphism. The kit includes at least two pairs of fluorescent oligonucleotide probes (i.e. a first FRET oligonucleotide pair and a second FRET oligonucleotide pair) wherein the oligonucleotides of each pair (a donor and acceptor oligonucleotide probe) are designed to hybridize to adjacent regions of nucleic acid sequences.

In one embodiment, the kit comprises a mixture of a first donor oligonucleotide probe, a first acceptor oligonucleotide probe, a second donor oligonucleotide probe and second acceptor oligonucleotide probe, wherein said first and second donor oligonucleotide probes are labeled with the same donor fluorophore and said first and second acceptor oligonucleotide probes are labeled with the same acceptor fluorophore. The first donor oligonucleotide probe and first acceptor oligonucleotide probe are designed to hybridize to adjacent regions of a first locus of a nucleic acid sequence wherein the hybridized set of first donor and first acceptor oligonucleotides are characterized as having a first melting temperature. The second donor oligonucleotide probe and second acceptor oligonucleotide probe are designed to hybridize to adjacent regions of a second locus of the nucleic acid sequence wherein the hybridized set of second donor and second acceptor oligonucleotides are characterized as having a second melting temperature. Furthermore the oligonucleotide probes are designed so the first melting temperature of the set of first donor oligonucleotide probe and first acceptor oligonucleotide probe is different from the second melting temperature of the set of second donor oligonucleotide probe and second acceptor oligonucleotide probe.

In one embodiment the kit comprises additional sets of FRET oligonucleotide pairs, wherein the additional sets of FRET oligonucleotide pairs have melting temperatures distinct from the first and second FRET oligonucleotide pairs.

Alternatively, in one embodiment the additional sets of FRET oligonucleotide pairs are labeled with a fluorescence resonance energy transfer pair whose acceptor fluorophore's emission does not overlap with the emission of the acceptor fluorophore of the first and second FRET oligonucleotide pairs. In one embodiment the additional sets of FRET oligonucleotide pairs include a mixture of FRET oligonucleotide pairs that have melting temperatures distinct from the first and second FRET oligonucleotide pairs as well as FRET oligonucleotide pairs labeled with fluorescence resonance energy transfer pairs whose acceptor fluorophores' emission does not overlap with the emission of the acceptor fluorophore of the first and second FRET oligonucleotide pairs.

In addition to the probes, the kit may contain one or more pairs of oligonucleotide primers designed to amplify one or more selected segments of nucleic acid. Alternatively, the kit may contain all of the reagents necessary to begin the PCR amplification reaction and fluorescent detection of mutations and polymorphisms.

In accordance with one embodiment of the present invention, multiplex PCR amplification and genotyping by fluorescent probe $T_m$ is used to simultaneously detect multiple variants in the hereditary hemochromatosis gene. Hereditary hemochromatosis is the most common genetic illness known in the Northern Hemisphere with more than 1 million Americans estimated to be at risk for the disease. This autosomal recessive disorder of iron metabolism occurs with a frequency of approximately 0.5% in Caucasian populations. The malregulation of intestinal iron absorption can eventually lead to parenchymal cell damage and end organ dysfunction. Long-term complications of iron overload include arthritis, cardiomyopathy, diabetes, cirrhosis, and hepatocellular cancer. The morbidity associated with iron overload is preventable through early diagnosis and treatment by phlebotomy.

A cysteine to tyrosine amino acid substitution, caused by a G845A transition at codon 282 (C282Y), is found on 85–100% of disease chromosomes from patients of northern European ancestry who meet well-defined clinical criteria for iron overload. Another mutation (H63D) is created by a C187G transversion. This substitution has an estimated penetrance between 0.44–1.5% of the homozygous C282Y genotype.

Current methods for genotyping the C282Y and H63D hemochromatosis causing mutations include oligonucleotide ligation, allele-specific oligonucleotide hybridization, and PCR-restriction fragment length analysis. All these methods require multiple manual steps and are time consuming. The use of PCR based technology in combination with real-time analysis by fluorescent melting curves provides homogenous amplification and genotyping in about 45 min. In one embodiment analysis of loci carrying the hemocromatosis mutations is conducted using a 3'-fluorescein labeled probe and a 5'-Cy5 labeled probe that are in fluorescence energy transfer when hybridized to the same strand (See Example 8).

One hundred and seventeen patients who met clinical criteria for iron overload and 56 normal controls were selected for analysis of the C282Y and H63D mutations in the HFE gene. Both groups were Caucasian Americans from Utah and neighboring states. Four different alleles could be identified simultaneously during melting curve analysis. The results of this study are summarized in Table 3.

TABLE 3

Analysis of the C282Y and H63D Mutations within the Utah Population

| Genotype* | | Patents with Iron Overload | | Control | |
|---|---|---|---|---|---|
| C282Y | H63D | N | % | N | % |
| hh | HH | 98 | 83.8 | 0 | 0 |
| Hh | HH | 4 | 3.4 | 7 | 12.5 |
| Hh | Hh | 4 | 3.4 | 0 | 0 |
| HH | HH | 6 | 5.1 | 38 | 67.9 |
| HH | Hh | 4 | 3.4 | 10 | 17.9 |
| HH | hh | 1 | 0.9 | 1 | 1.8 |
| Total | | 117 | | 56 | |

| | Allele Frequency (%) | |
|---|---|---|
| C282Y | 204/234 (87.1) | 7/112 (6.3) |
| H63D | 10/234 (4.3) | 12/112 (10.7) |

*hh designates homozygosity for the mutation.
Hh designates heterozygosity.
HH designates homozygous wild type.

Ninety-eight (83.8%) of the patients and none of the controls were homozygous for the C282Y mutation. The C282Y mutation was found in 87% of patient chromosomes and 6.3% of chromosomes from normal controls. The H63D mutation was found in 11% of control chromosomes and only 4.3% of patient chromosomes. There were 8 patients and 7 normal controls that were heterozygous for the C282Y mutation. One-half of the C282Y heterozygous patients carried the H63D mutation, whereas, there were no compound heterozygous genotypes among the controls. In addition, a single probe identified three alleles including an unexpected polymorphism (A193T), demonstrating the potential of adjacent fluorescent hybridization probes for scanning for known as well as unknown mutations.

EXAMPLE 1

Figure 2:
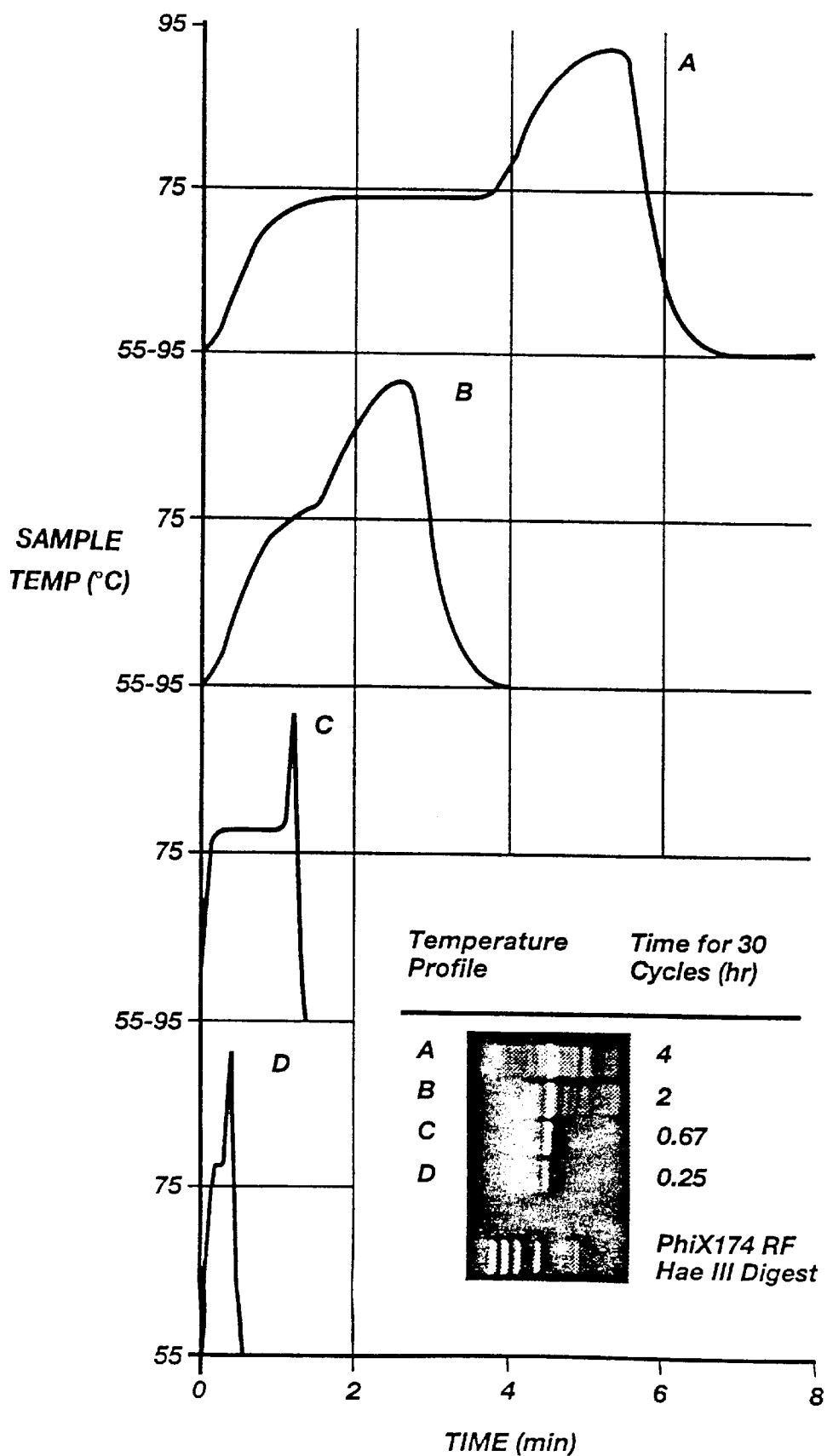
FIG. 2 shows the results of four different temperature/time profiles (A–D) and their resultant amplification products after thirty cycles (inset).

FIG. 2 shows the results of four different temperature/time profiles (A–D) and their resultant amplification products after thirty cycles (A–D). The profiles A and B in FIG. 2 were obtained using a prior art heating block device and a prior art microfuge tube. As can be seen in FIG. 2, the transitions between temperatures are slow and many nonspecific bands are present in profiles A and B. Profile B shows improvement in eliminating some of the nonspecific bands (in contrast to profile A) by limiting the time each sample remains at each temperature, thus indicating that shorter times produce more desirable results.

Profiles C and D were obtained using a rapid temperature cycler. As can be seen in FIG. 2, amplification is specific and, even though yield is maximal with 60-second elongation times (C), it is still entirely adequate with 10-second elongation times ()).

The optimal times and temperatures for the amplification of a 536 bp fragment of beta-globin from human genomic DNA were also determined. Amplification yields and product specificity were optimal when denaturation (93° C.) and annealing (55° C.) were less than 1 second. No advantage was observed when denaturation or annealing times were extended. The yield increased with longer elongation times at 77° C., but there was little change with elongation times longer than 10–20 seconds. Further information can be obtained from: C. T. Wittwer et al., Rapid Cycle Allele-Specific Amplification with Cystic Fibrosis delta F(508) Locus, 39 *Clinical Chemistry* 804 (1993) and C. T. Wittwer et al., Rapid DNA Amplification, THE POLYMERASE CHAIN REACTION 174 (1994), which are both now incorporated herein by this reference.

EXAMPLE 2

A 110 bp beta-globin fragment was amplified from 50 ng human genomic DNA using the human beta-globin primers PC03/PC04 (110 base pairs). Those primers are described in C. T. Wittwer et al., Automated polymerase chain reaction in capillary tubes with hot air, 17 Nucl. Acids. Res. 4353–4357 (1989), the disclosure of which is now incorporated herein by reference. DNA amplification was performed in 50 mM Tris, pH 8.5 (25° C.), 3 mM MgCl$_2$, 500 µg/ml bovine serum albumin, with the internal probes CAAACAGACA CCATGGTGCA CCTGACTCCT GAGGA-fluorescein (SEQ ID NO:1) and Cy5-GAAGTCTGCC GTTACTGCCC TGTGGGGCAA G-p (SEQ ID NO:2) at 0.2 µM each and 0.8 U KlenTaq1 polymerase (a 5'-exonuclease deficient variant of Taq polymerase—U.S. Pat. No. 5,436,149) in a 10 µl reaction. The probes hybridized internal to the primers on the same strand and were immediately adjacent without any intervening bases.

Probes and primers were synthesized by standard phosphoramidite chemistry as known in the art, using a Pharmacia Biotech Gene Assembler Plus (Piscataway, New Jersey). The 3'-fluorescein-labeled probe was synthesized on a fluorescein-labeled CPG cassette (Glen Research, Sterling, Va.) with the final trityl-ON to assist with C18 reverse phase HPLC purification. The late eluting peak was collected and the trityl group was removed on a PolyPack (Glen Research). The fluorescein-labeled oligo was eluted with 50% acetonitrile and again purified by C18 reverse phase HPLC. The 5'-Cy5-labeled probe was synthesized with a chemical phosphorylation agent on the 3'-end (Glen Research) and adding a Cy5 amidite (Pharmacia) to the 5'-end during trityl-OFF synthesis. Failure sequences were removed by C18 reverse phase HPLC. Probe purity was checked with polyacrylamide electrophoresis and the absorbance of the dye and the oligo.

HPLC was performed on a 4×250 mm Hypersil ODS column (Hewlett Packard) with a 0.1 M triethanolamine:acetate mobile phase and an acetonitrile gradient at 1 ml/min. The eluate was monitored for both absorbance ($A_{260}$) and fluorescence (490 nm excitation, 520 nm emission for fluorescein and 650 nm excitation, 670 nm emission for Cy5). Tritylated- and fluorescein-labeled oligonucleotides were eluted with a 10–20% acetonitrile gradient, and Cy5-labeled oligonucleotides eluted over a 10–40% acetonitrile gradient.

Figure 11B:
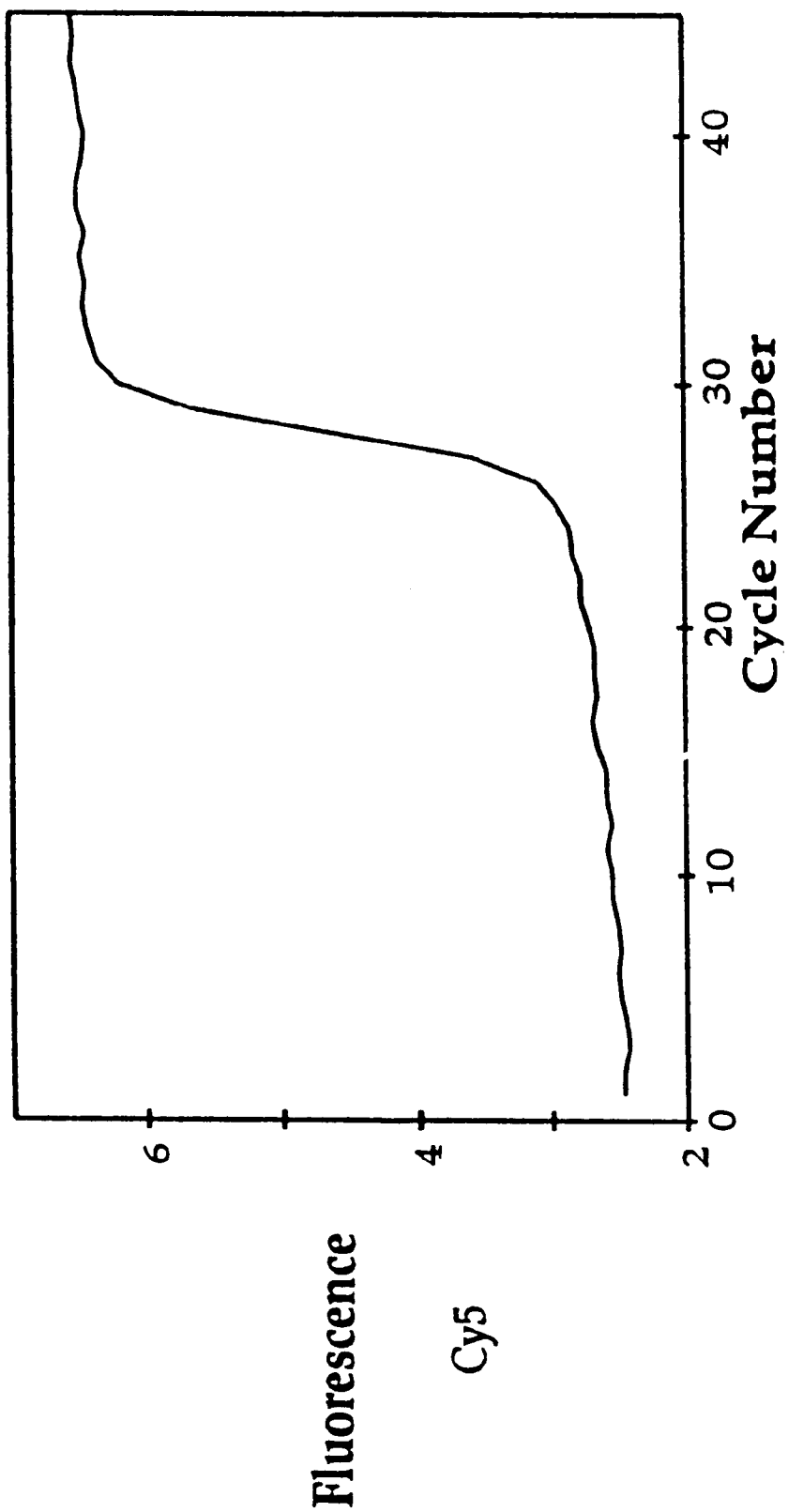
FIG. 11 shows resonance energy transfer occurring between fluorescein- and Cy5-labeled adjacent hybridization probes at each cycle during PCR.
Figure 11C:
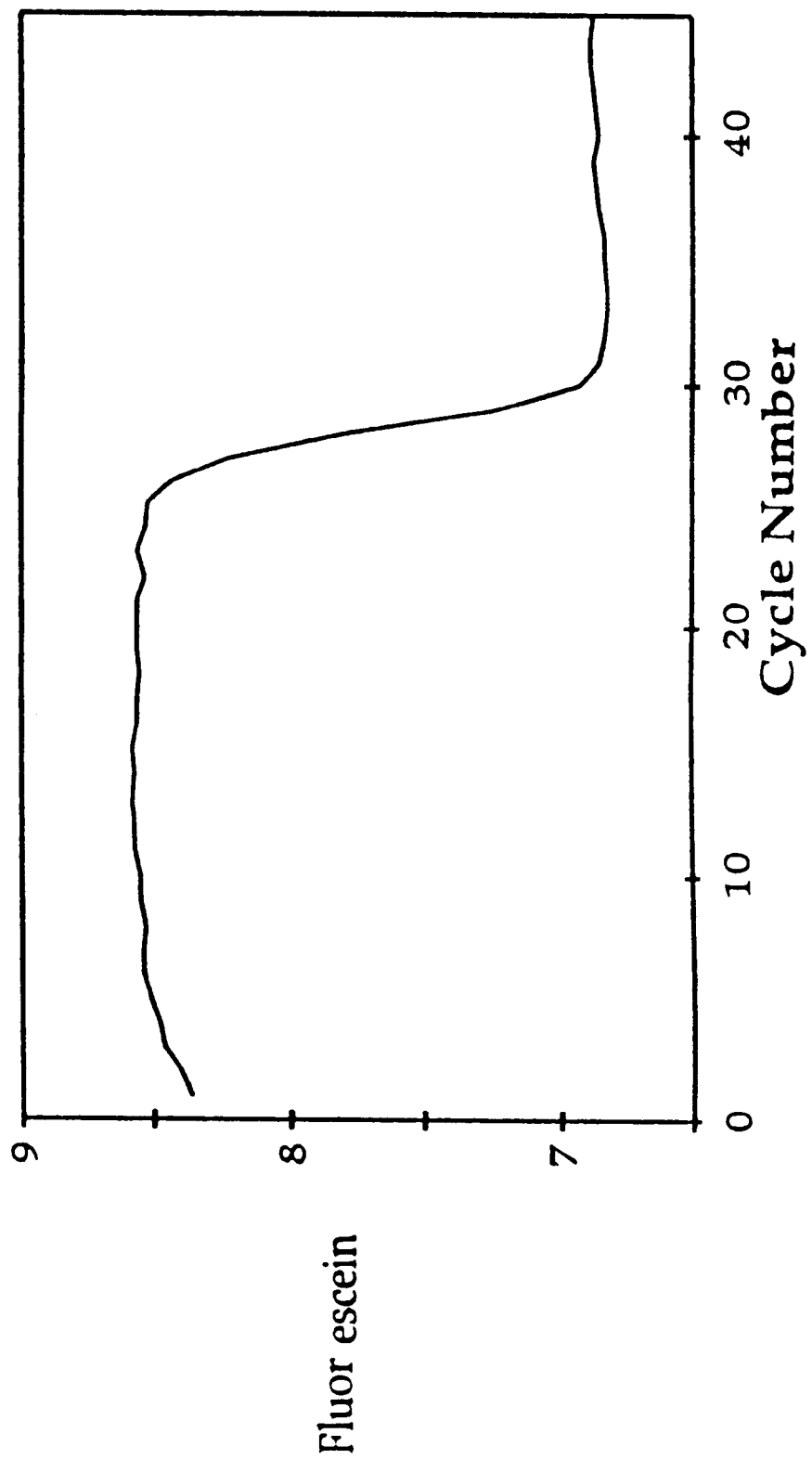

Temperature cycling was 94° C. for 0 sec with a programmed approach rate of 20° C./sec, 60° C. for 20 sec with an approach rate of 20° C./sec, and 75° C. for 0 sec with an approach rate of 1° C./sec in a capillary fluorescence rapid temperature cycler. During temperature cycling, fluorescein and Cy5 fluorescence were acquired each cycle at the end of the annealing/extension segment. Resonance energy transfer was observed as both a decrease in fluorescein fluorescence, and an increase in Cy5 fluorescence beginning around cycle 26 of amplification (FIGS. 11A–11C). In general, observing the fluorescence ratio of Cy5 to fluorescein fluorescence is preferred.

EXAMPLE 3

The effect of the ratio, concentration, and spacing of fluorescein and Cy5-labeled adjacent hybridization probes during PCR was studied. Amplification of the beta globin locus and probe pair of Example 2 was used and the maximum change in the fluorescence ratio of Cy5 to fluorescein was observed. The maximal signal occurred when the ratio of Cy5 to fluorescein-labeled probes was 2:1. At this 2:1 ratio, the best signal occurred at a fluorescein probe concentration of 0.2 µM and a Cy5-labeled probe concentration of 0.4 µM. The optimal number of intervening bases between adjacent hybridization probes during PCR was also determined. Several probes of the same length but slightly shifted in their hybridization position were synthesized according to Example 2 so that when they hybridized to the beta globin target, 0, 1, 2, 3, 4, or 6 bases remained between the probes. The highest signal during PCR occurred with one intervening base. Although some resonance energy transfer was detected at a spacing of 15 and even 25 bases, much better transfer occurred at 0–5 bases.

EXAMPLE 4

Cycle-by-cycle monitoring of PCR was performed by resonance energy transfer between a Cy5-labeled primer and a fluorescein-labeled hybridization probe. This was compared to monitoring with adjacent Cy5/fluorescein hybridization probes. The Cy5-labeled primer was CAACT-TCATC CACGT*TCACC (SEQ ID NO:3) where T* is a modified T base with Cy5 attached and the corresponding probe was GTCTGCCGTT ACTGCCCTGT GGGGCAA-fluorescein (SEQ ID NO:4). The adjacent hybridization probes were CCTCAAACAG ACACCATGGT GCACCT-GACT CC-fluorescein (SEQ ID NO:5) and Cy5-GAAGTCTGCC GTTACTGCCC TGTGGGGCAAp (SEQ ID NO:6). The hybridization probes were synthesized according to Example 2 and used at 0.2 µM. The Cy5-labeled primer was synthesized in two steps. Automated synthesis was used to incorporate an amino-modifier C6dT (Glen Research) at the desired T position. Then, the monovalent N-hydroxysuccinimide ester of Cy5 (FIG. 4) was manually conjugated to the amino linker according to the manufacturer's instructions (Amersham). HPLC purification was as described in Example 2.

Figure 12:
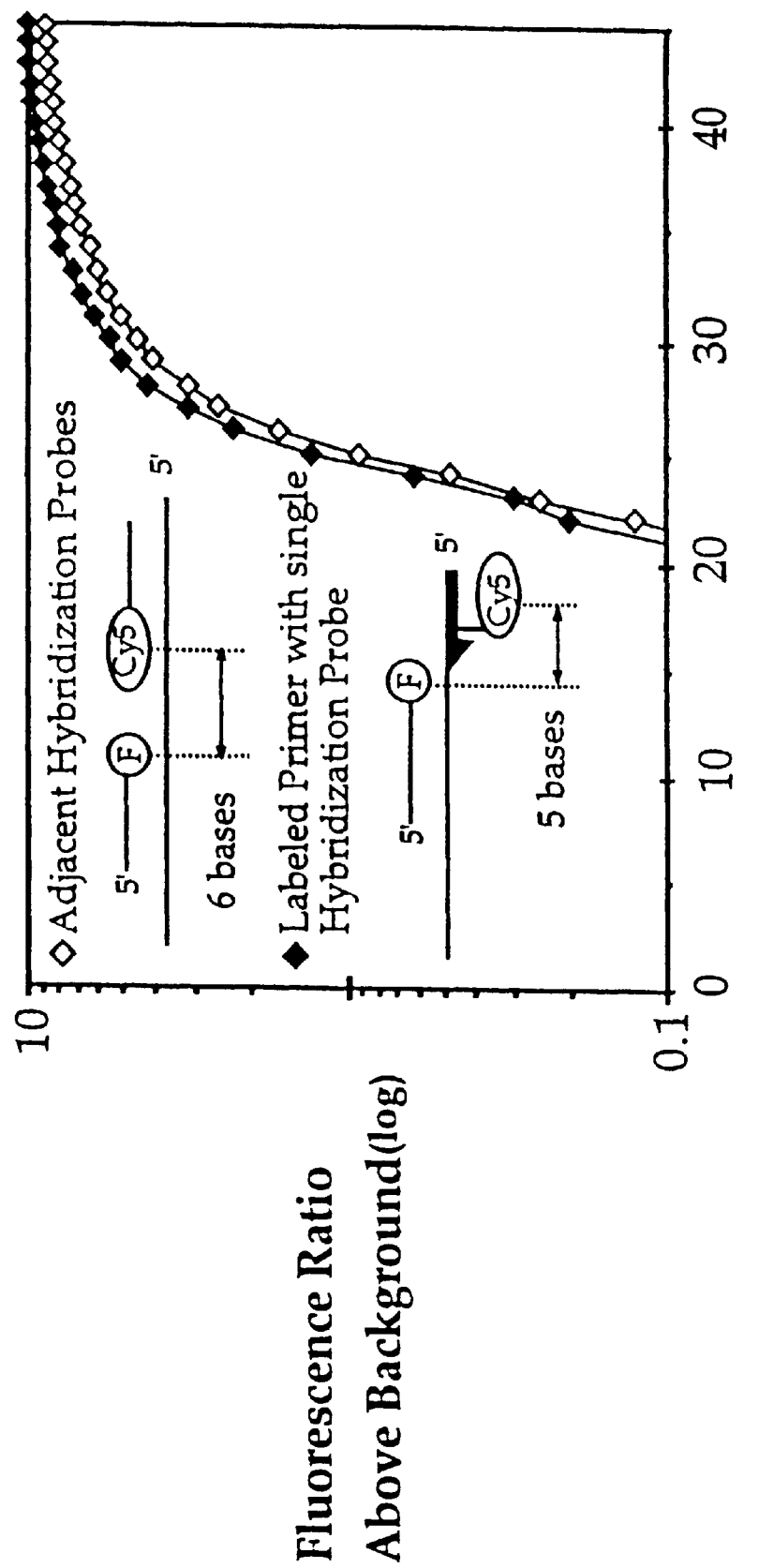
FIG. 12 is a fluorescence ratio v. cycle number plot distinguishing two hybridization probe designs monitored by resonance energy transfer: (◇) two hybridization probes labeled respectively with fluorescein and Cy5; and (♦) a primer labeled with Cy5 and a probe labeled with fluorescein.

The Cy5-labeled primer (0.5 µM) was used instead of PCO4 to amplify the 110 base pair beta-globin fragment from human genomic DNA as in Example 2, except that 0.4 U of Taq polymerase was used per 10 µl. The adjacent hybridization probes also monitored amplification of the same beta-globin fragment. Temperature cycling was done at 94° C. for 0 sec and 60° C. for 20 sec. The fluorescence was monitored once each cycle at the end of the annealing/extension segment. In both methods, fluorescence energy transfer to Cy5 increases with hybridization and is plotted as a ratio of Cy5 to fluorescein fluorescence (FIG. 12).

EXAMPLE 5

While fluorescence monitoring during PCR can be done once each cycle at a constant temperature, the present invention provides the important advantage of providing continuous monitoring throughout the PCR cycle, thus allowing for dynamic monitoring of fluorescence as the temperature changes. In this manner mutations and polymorphisms can be detected by determining the melting temperature of added fluorescently labeled hybridization probes.

The factor V Leiden mutation is a single base change (G to A) that substitutes a glutamine residue for an arginine residue at amino acid residue 506 (R506Q). For further information, see R. M. Bertina et al., Mutation in Blood Coagulation Factor V Associated with Resistance to Activated Protein C, 369 Nature 64–67 (1994) and J. Voorberg et al., Association of Idiopathic Venous Thromboembolism with a Single Point-Mutation at Arg$^{506}$ of Factor V, 343 Lancet 1535–36 (1994), both of which are hereby incorporated by reference. As used herein, "factor V Leiden mutation locus" means the nucleotide position in the factor V gene at which a guanine base in the wild type is replaced by an adenine base in the factor V Leiden mutant. SEQ ID NO:7 shows a portion of the wild type factor V gene, and SEQ ID NO:8 shows the corresponding portion of the factor V Leiden gene, with the relevant nucleotide at position 31 in each case. The complete nucleotide sequence of the factor V gene is described at R. J. Jenny et al., Complete cDNA and Derived Amino Acid Sequence of Human Factor V, 84 Proc. Nat'l Acad. Sci. USA 4846–50 (1987), hereby incorporated by reference, and the sequences can also be obtained at Genbank locus HLMF10. The amino acid change in the mutant factor V protein makes this clotting factor resistant to degradation and increases the tendency to clotting and thrombosis. As the most common cause of inherited thrombophilia, this mutation is the target of a common laboratory test done in clinical molecular genetics laboratories.

The standard method of analysis for the factor V Leiden mutation is to amplify the gene segment by PCR, digest the resulting amplified products with a restriction endonuclease that cuts the wild type sequence but not the mutant; and distinguish digested wild type and undigested mutant products by gel electrophoresis. This is a method well known in the art for analysis for defined mutations. Such a test usually requires about 4 hours, including PCR amplification (2 hours), enzyme digestion (1 hour), and electrophoresis (1 hour). Post-amplification steps include opening the sample tube, adding the enzyme, and transferring the digested sample to the electrophoresis apparatus. Post-amplification processing increases the risk of end product contamination, and manual handling requires care to prevent mislabeling of samples. A method that simultaneously amplifies and analyzes for point mutations would eliminate these concerns.

A method for complete amplification and analysis of the factor V Leiden mutation within 30 min in the same instrument comprises asymmetrically amplifying a portion of a human genomic DNA sample containing the mutation locus, followed by obtaining and analyzing a melting curve for the amplified DNA. Genomic DNA is prepared according to methods well known in the art, and preferably, the melting curve is obtained by a resonance energy transfer methodology using a fluorogenic hybridization probe. Such an assay easily discriminates between homozygous wild type, homozygous mutant, and heterozygous genotypes. In one embodiment, the oligonucleotide probe is 3'-labeled with fluorescein and designed to hybridize on the amplified DNA near to a Cy5-labeled primer for resonance energy transfer. This method can be applied to any defined mutation.

PCR amplification was carried out in 10 µl reaction mixtures comprising 50 mM Tris, pH 8.3, 3 mM MgCl$_2$, 500 µg/ml bovine serum albumin, 200 µM each dNTP, 0.5 µM Cy5-labeled primer (SEQ ID NO:9), 0.2 µM unlabeled opposing primer (SEQ ID NO: 10), 0.1 µM fluorescein-labeled probe (SEQ ID NO:11), 0.4 U Taq polymerase, and fifty ng human genomic DNA. Four different samples of DNA were tested: human genomic DNA from an individual homozygous for the factor V Leiden mutation; human genomic DNA from a heterozygous individual; human genomic DNA from an individual homozygous for the wild type factor V allele; and a negative control without DNA. The orientation of the Cy5-labeled primer, the fluorescein-labeled probe, and the mutation site (identified by asterisk) are shown below:

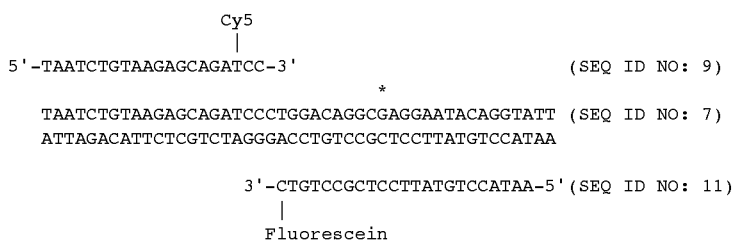

The sequence of the unlabeled opposing primer was TGT-TATCACACTGGTGCTAA (SEQ ID NO:10) and the amplified product was 186 base pairs in length. The Cy5-labeled primer was obtained as in Example 4. Cycling conditions were 94° C. for 0 sec (slope=20), 50° C. for 10 sec (slope=20), and 72° C. for 0 sec (slope=1) for 50 cycles, followed by cooling to 45° C. and continuous fluorescence monitoring at a slope of 0.2° C./sec to 94° C. for the melting curve. The closer the Cy5 label is to the primer's 3'-end, the greater the resonance energy transfer signal. However, the 3'-end must have a free 3'-hydroxyl for polymerase extension, and placing the Cy5 too close to the 3'-end (either on the 3' or penultimate base) may inhibit polymerase attachment and extension. The 3'-fluorescein probe should hybridize as close to the primer as possible (minor overlap of 1–3 bases can be tolerated) and the mutation site should be near the middle of the probe. A 5-base separation between the hybridized fluorophores and a mutation at base 8 of a 23-mer probe gave a melting curve shift of 8° C. between mutant and wild type sequences (FIGS. 13A and 13B).

Figure 13A:
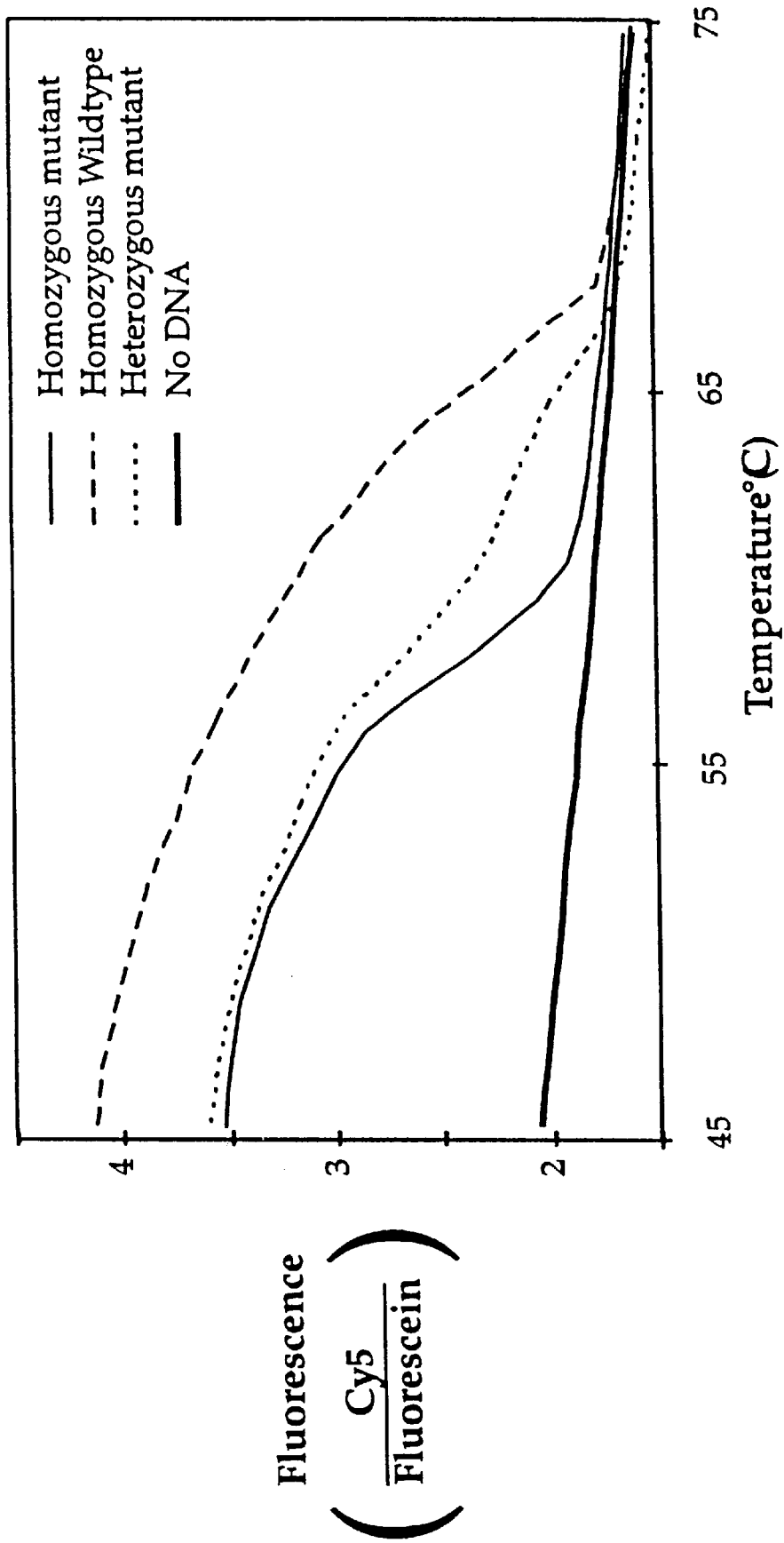
FIGS. 13A and 13B show (A) melting curves and (B) melting peaks for PCR products of a person heterozygous for the factor V Leiden mutation (solid line), homozygous for the factor V Leiden mutation (dotted line), homozygous wild type (broken line), and no DNA control (alternating dot and dash).
Figure 13B:
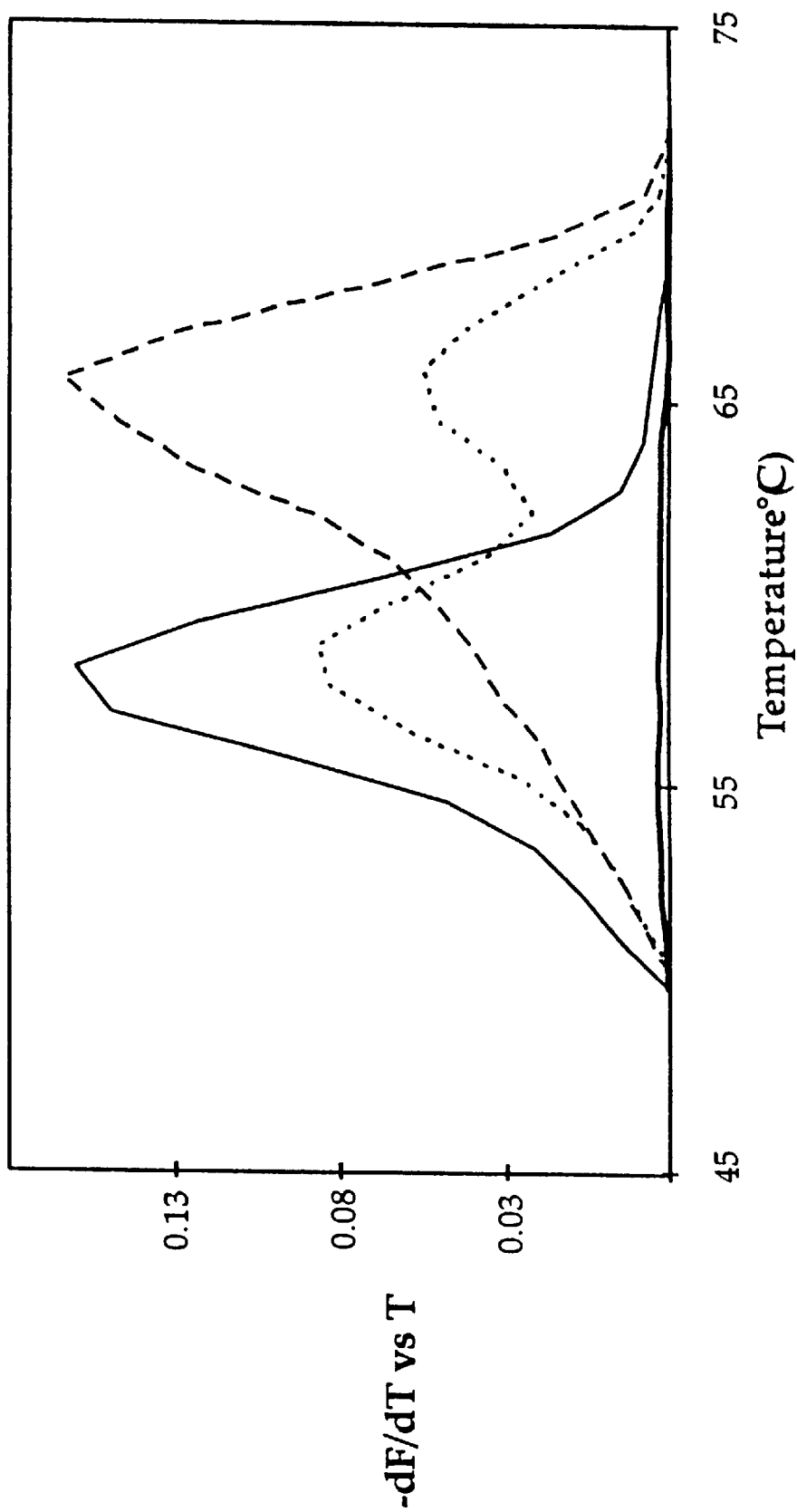
Figure 14:
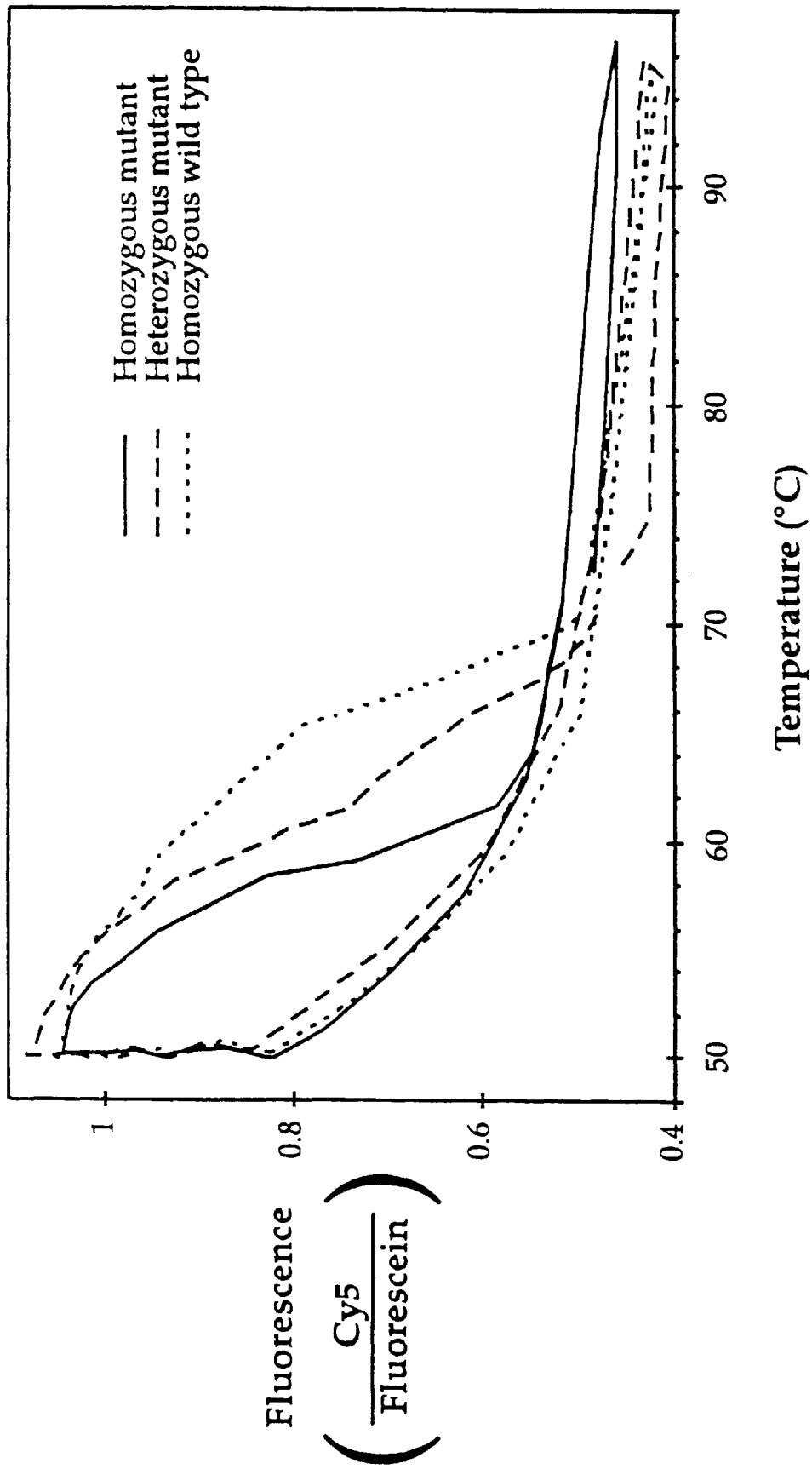
FIG. 14 shows a fluorescence ratio v. temperature plot of continuous monitoring during cycle 40 of PCR products of a sample homozygous for the factor V Leiden mutation (solid line), heterozygous for the factor V Leiden mutation (dotted line), and homozygous wild type (alternating dot and dash).

The highest quality melting curves were obtained at the end of amplification with a slow temperature transition rate (0.2° C./sec), see FIG. 13A although monitoring during each cycle at 1° C./sec between 50° C. and 94° C. also provided clear genotype identification (FIG. 14). The melting curves are easiest to visualize by plotting the negative derivative of fluorescence with respect to temperature vs temperature (−dF/dT vs T), see FIG. 13B. Such a plot allows facile visual identification of all possible genotypes from the raw fluorescence data.

It will be appreciated that the particular probes and primers disclosed herein for detection of the factor V Leiden mutation are merely illustrative, and that a person of ordinary skill in the art will be able to design other probes and primers for detection of mutations without undue experimentation by following the principles and guidelines set forth herein. Although fluorescein and Cy5 were used as resonance energy transfer labels in the example above, other acceptors, such as Cy5.5, can also be used with fluorescein.

EXAMPLE 6

The factor V locus of Example 5 was amplified as before except that the primer was labeled with Cy5.5 instead of Cy5. Cy5.5 emission was observed through a 683 nm long pass dichroic and a 683–703 nm bandpass interference filter. The Cy5.5 to fluorescein ratio increased above background at about cycle 30 and the ratio approximately doubled by 50 cycles of asymmetric amplification. When amplified with wild type DNA, the probe Tm was 65–66° C. as judged by melting peaks.

EXAMPLE 7

Figure 15:
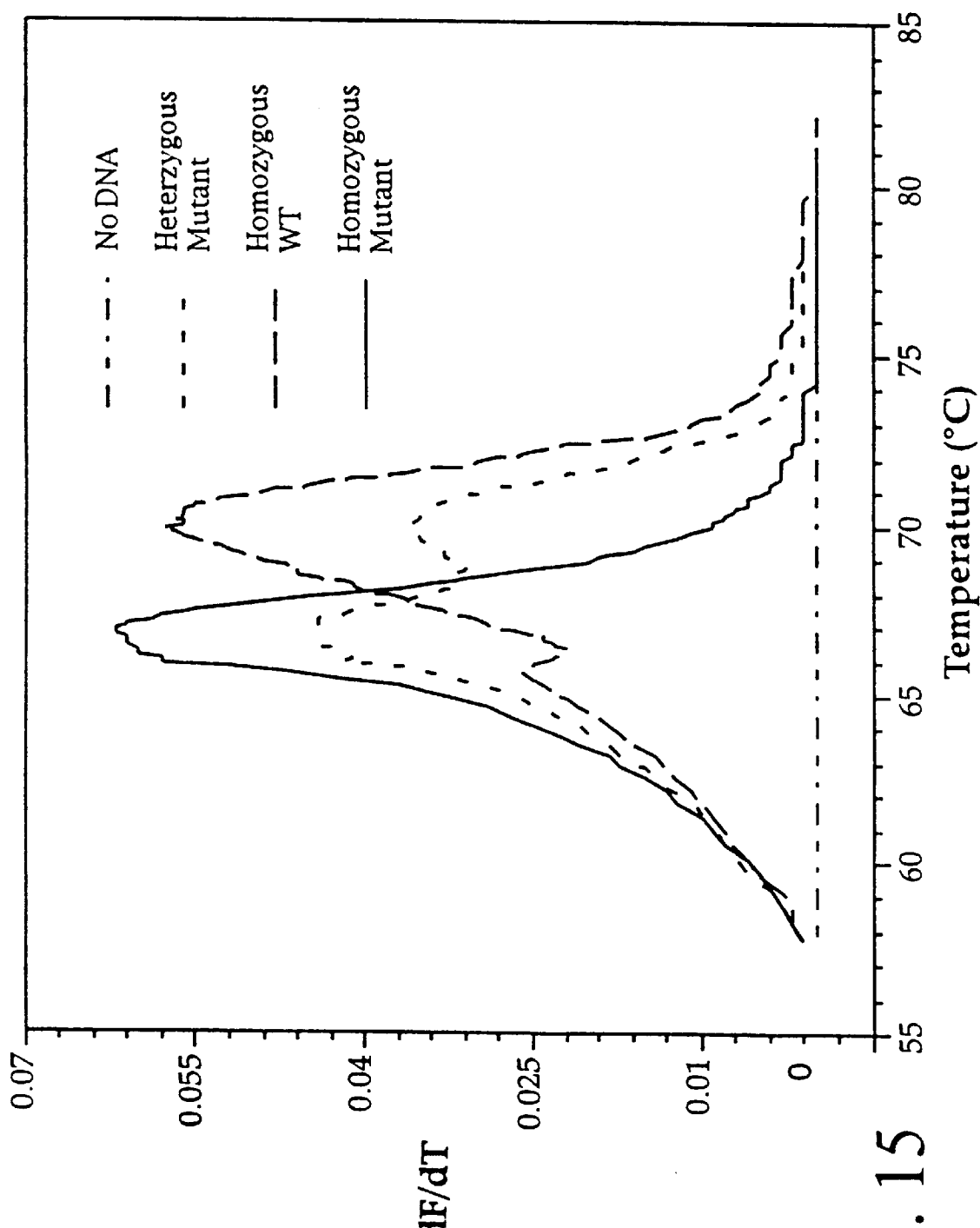
FIG. 15 shows melting peaks of a homozygous mutant of the methylenetatrahydrofolate gene (solid line), homozygous wild type (broken line), heterozygous mutant (dotted line), and no DNA control (alternating dot and dash).

There is a common point mutation in the methylenetetrahydrofolate reductase (MTHFR) gene ($C_{677}T$) that converts an alanine to a valine residue and results in a thermolabile enzyme. This mutation can reduce MTHFR activity and lead to elevated homocysteine plasma levels which has been implicated as an independent risk factor for early vascular disease and thrombosis as is well known in the art. One of the primers was labeled with Cy5 (TGAAGGAGAAGGTGTCT*GCGGGA) (SEQ ID NO:12) where T* represents a modified T residue linked to Cy5. The probe sequence was fluorescein-CCTCGGCTAAATAGTAGTGCGTCGA (SEQ ID NO:13) and the other primer was AGGACGGTGCGGTGAGAGTG (SEQ ID NO:14). A 198 base pair fragment of the MTHFR gene was amplified from 50 ng of human genomic DNA in 50 mM Tris, pH 8.3, 2 mM MgCl$_2$, 500 μg/ml bovine serum albumin, 0.2 mM of each dNTP, 0.5 μM of the Cy5-labeled primer, 0.1 μM of the opposing primer, 0.1 μM of the fluorescein-labeled probe, and 0.4 U Taq DNA polymerase per 10 μl. Each cycle was 30 sec long and consisted of denaturation at 94° C. followed by a 20 sec combined annealing/extension step at 60° C. The temperature transition rate between steps was 20° C./sec. After 60 cycles, a melting curve was acquired as follows: heating from 50–65° C. at 0.5° C./sec, 65–75° C. at 0.1° C./sec, and 75–94° C. at 0.5° C./sec. After baseline subtraction and conversion to melting peaks, all possible genotypes were easily distinguished (FIG. 15).

EXAMPLE 8

Multiplex Analysis of the Hemochromatosis Gene

Samples

Genomic DNA from Caucasian individuals was collected over a 10-year period for studying hemochromatosis pedigrees in Utah and neighboring states. Methods of collection were approved by the institutional review board at the University of Utah. Two clinically defined subject groups consisting of 117 patients and 56 controls were selected from 250 genotyped samples in order to determine the prevalence of the C282Y and H63D mutations in the HFE gene. Family-based controls had either married into a pedigree or had no HLA identity with the proband. Genotyped patients with ambiguous clinical histories were excluded from the subject group. Patients were selected through laboratory evidence of iron overload (transferrin saturation >55% and serum ferritin >600 μg/liter), and liver biopsies were performed on most of these patients to determine the grade of liver siderosis. All controls had normal values for serum ferritin and percent transferrin saturation.

Genotyping

All samples were genotyped at the C282Y and H63D sites with adjacent fluorescent hybridization probes. Genotyping both sites simultaneously by multiplexing was performed on 70 samples. Reagent concentrations for multiplexing and single-site analysis were the same. However, multiplexed reactions contained 2 primer sets and 2 fluorescently-labeled probe sets. Each 10 μL reaction contained 50 mM Tris, pH 8.3 (25° C.), 500 μg/ml bovine serum albumin, 0.2 mM each deoxyribonucleoside triphosphate, 4 mM MgCl$_2$, 0.5 μM each primer, 0.1 μM site-specific 3'-fluorescein labeled probe, 0.2 μM site-specific 5'-Cy5 labeled probe, 50 ηg genomic DNA, and 0.4 U native Taq DNA polymerase. Samples were loaded into separate plastic/glass composite cuvettes, centrifuged and capped. Homogenous PCR and melting curve acquisition used a 24 sample rapid fluorescent thermal cycler (LightCycler LC24, Idaho Technology, Idaho Falls, Id.).

Forty repeats of a 2-temperature cycle were performed (94° C. for 0 s and 62° C. for 20 s with programmed transitions of 20° C./s). Fluorescence was acquired once each cycle for 50 msec per sample at the end of the combined annealing/extension step. An appended analytical cycle after amplification allowed immediate genotyping by derivative melting curves. The genotyping protocol included denaturation at 94° C. for 20 s; annealing for 20 s each at 65° C., 55° C. and 45° C. (C282Y, S65C and multiplexing) or 75° C., 65° C., and 55° C. (H63D); and a high resolution melting transition to 75° C. at a rate of 0.1° C./s. Cy5 (655–695 nm) and fluorescein (520–560 nm) fluorescence were monitored for 50 msec per sample at each 0.1° C. temperature increment.

The data collected during the melting phase were used to genotype each sample. Melting curves were generated by plotting Cy5/fluorescence (F) vs temperature (T). Easily discriminated melting peaks were obtained by plotting the same data as –dF/dT vs temperature.

Genotyping performed in the LightCycler™ (Idaho Technology, Idaho Falls, Id.) was compared to conventional PCR-restriction fragment length analysis. PCR-restriction fragment length analysis was performed on all samples for the C282Y mutation and on 40 random samples for the H63D mutation. Amplification for the PCR-restriction fragment length method was performed in an air thermal cycler (RapidCycler™, Idaho Technology, Idaho Falls, Id.) using the same primers, $MgCl_2$ concentration and temperature parameters as that used in the LightCycler™. Probes were not added for PCR-restriction fragment length analysis. Samples were restriction digested at C282Y or H63D by adding 1 μL of either SnaBI (4 U/μl, New England Biolabs, Beverly, Mass.) or Bcl I (10 U/μgl, New England Biolabs), respectively, to 1 μL of the recommended digestion buffer and 8 μL of amplicon. The samples were incubated for 2 hours at either 37° C. (SnaBI) or 50° C. (Bcl I) and products were visualized by ethidium bromide staining after separation on a 1.5% agarose gel at 5 V/cm for 60 min.

Sequencing

Four samples were sequenced for identification of the A193T polymorphism. PCR products were sequenced Model 377, Perkin-Elmer, Foster, Calif.) from TOPO TA plasmid vectors (TOPO TA Cloning®, Invitrogen, Calif.).

through a 4×250-mm Hypersil ODS column (Hewlett Packard, Fullerton, Calif.) using 0.1 M triethylammonium acetate, pH 7.0 and a 20–60% (fluorescein probe) or 40–80% (Cy5 probe) gradient of acetonitrile (1 ml/min). The eluate was monitored with tandem absorbance and fluorescence detectors (Waters 486 and 474, Milford, Mass.). Fractions with both A260 and fluorescence peaks were collected.

Primer/Probe Design

The HFE cDNA sequence was used for selection of primers and probes (Genbank Accession M31944). Primers and probes were chosen using Primer Designer for Windows™ (Scientific and Educational Software, State Line, Pa., USA). Primers for both mutation sites were selected with similar $T_m$s and GC content to allow multiplexing. The longer 5'-Cy5 labeled probes were designed with at least a 15° C. higher $T_m$ than the 3'fluorescein labeled probes that span the area targeted for mutation detection. In this way a Cy5-labeled probe acts as an "anchor" and remains annealed to the single-stranded amplicon while the fluorescein-labeled probe is heated through the characteristic $T_M$ for that allele. The fluorescein-labeled probes were designed to have Tms that would allow differentiation of all 4 alleles by melting peak analysis. The primer and probe sequences are shown in Table 1.

TABLE 1

Primer and Probe Sequences Used for Genotyping the HFE Gene

| Codon | Forward Primers | Reverse Primers |
|---|---|---|
| C282Y | TGGCAAGGGTAAACAGATCC (SEQ ID NO. 15) | CTCAGGCACTCCTCTCAACC (SEQ ID NO. 16) |
| H63D | CACATGGTTAAGGCCTGTTG (SEQ ID NO. 17) | GATCCCACCCTTTCAGACTC (SEQ ID NO. 18) |

| Codon | Fluorescent Probes |
|---|---|
| C282Y | AGATATACGTACCAGGTGGAG-Fluorescein* (SEQ ID NO. 19) |
|  | Cy5-CCCAGGCCTGGATCAGCCCCTCATTGTGATCTGGG-P** (SEQ ID NO. 20) |
| H63D | CGTGTTCTATGATGATGAGAGTCGCCG-Fluorescein* (SEQ ID NO. 21) |
|  | Cy5-GGAGCCCCGAACTCCATGGGTTTCCAGTAGAATTTCAAGCCAGAT-P** (SEQ ID NO. 22) |

*Nucleotide bases involved in duplex mismatch formation are underlined.
**P indicates the addition of a phosphate group.

Primer/Probe Synthesis

Primers for the C282Y codon and the H63D codon were synthesized by standard phosphoramidite chemistry (Pharmacia Biotech Gene Assembler Plus, Piscataway, N.J.). The 3'-fluorescein labeled probes were synthesized on fluorescein-controlled pore glass cassettes (BioGenics, San Ramon, Calif.). A 5'-trityl group was retained on the fluorescein labeled probes for purification of full-length sequences. Detritylation was performed on a Polypack column (Glen Research, Sterling, Va.) and the labeled oligo eluted with 50% acetonitrile. The 5'-Cy5 probes were synthesized using a Cy5 phosphoramidite (Pharmacia Biotech) and a chemical phosphorylation reagent (Glen Research) to prevent extension from the 3'-end of the probe.

Purity of probe synthesis was determined by calculating the ratio of fluorophore concentration to oligonucleotide concentration. Probes with ratios outside 0.8–1.2 were further purified by reverse-phase C18 high-pressure liquid chromatography. Labeled oligonucleotides were passed Empirical melting temperatures for the 3'-fluorescein probe/allele duplexes are shown in Table 2.

TABLE 2

Emperical Melting Temperatures for Fluorescein Probe/Allele Duplexes

| Condon | Allele | Duplex Tm |
|---|---|---|
| C282Y | G845 | 53° C. |
|  | 845A | 60° C. |
| H63D | C187 | 63° C. |
|  | 187G | 68.5° C. |
|  | C187/193T | 58.5° C. |

Results

Figure 16:
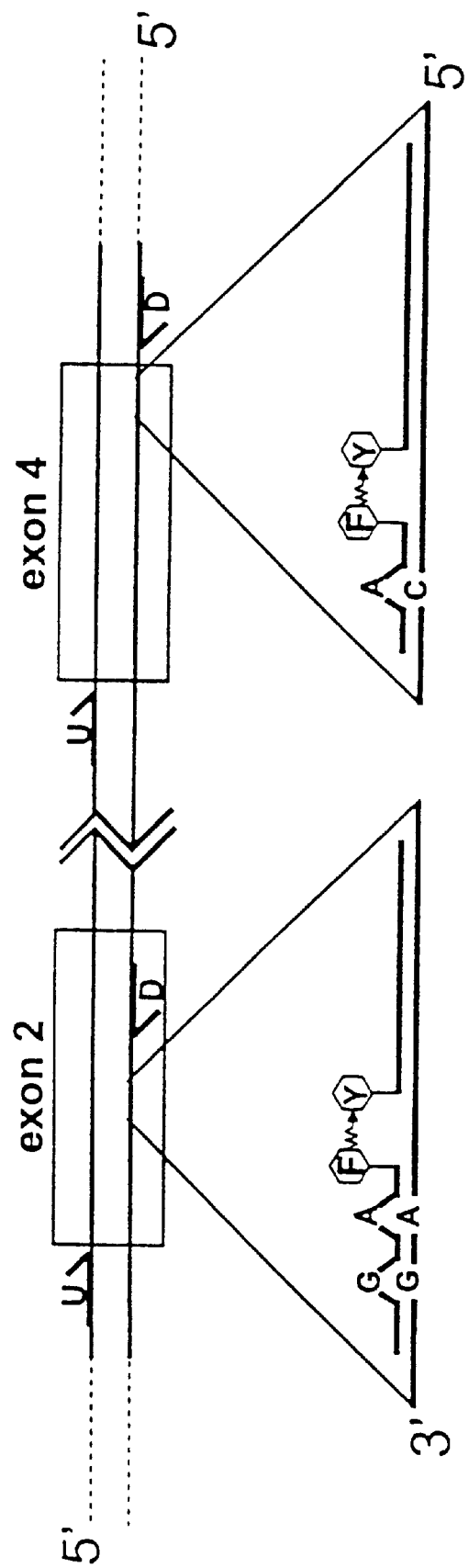
FIG. 16 is a schematic representation showing primer and probe placement for multiplex amplification and genotyping of HFE. Upstream (U) and downstream (D) primers are illustrated with respect to exon boundaries. Regions of exon 2 and exon 4 were amplified for analysis of the H63D (C187G) and C282Y (G845A) mutations, respectively. The fluorescein (F) labeled probes are in fluorescence resonance energy transfer with the more thermally stable Cy5 (Y) labeled probes. The fluorescein labeled probes form a single mismatch when hybridizing to the singe-stranded wild type allele. The probe hybridizing within exon 2 forms two mismatches when hybridizing to a wild type (C187) allele containing the S65C (193T) polymorphism.

Genotyping with adjacent fluorescent hybridization probes A schematic representation of the adjacent fluorescent hybridization probes used for genotyping the HFE locus is shown in FIG. 16. The 3'-fluorescein labeled probes spanning the C282Y and H63D sites were 21 and 27 base pairs long, respectively. These probes were designed so that during hybridization each probe formed a mismatch with the wild type allele extended by the downstream primer. Table I shows the positions of the potential probe mismatches.

Figure 17:
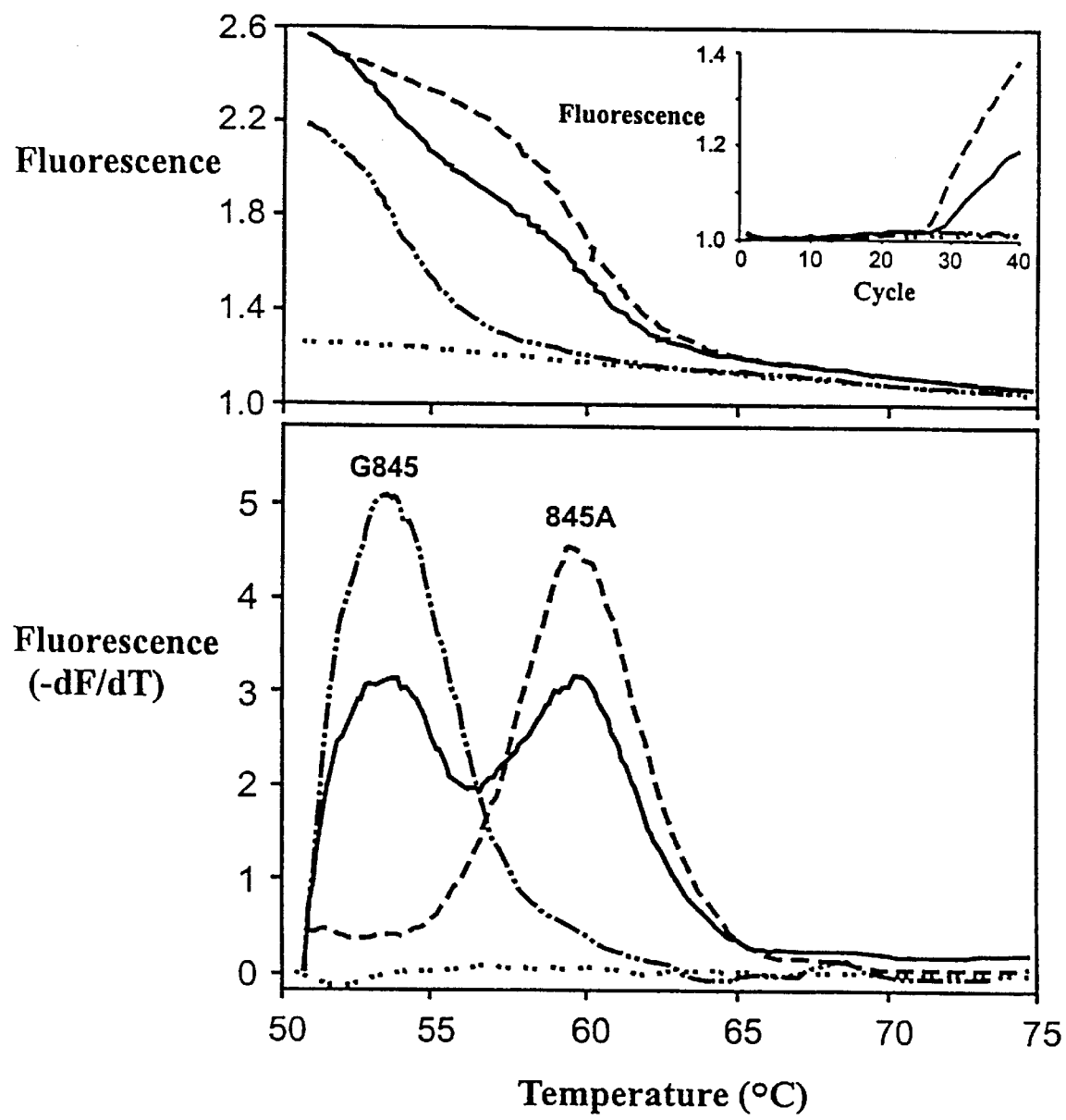
FIG. 17 shows a real-time amplification and genotyping of the C282Y site. The inset shows amplification (Cy5 fluorescence vs cycle number) of the genotypes: homozygous wild type (— -- —), heterozygous C282Y (—), homozygous C282Y (— — —). A no template control (-- -- --) is also included. Data for amplification and melting curve analysis were normalized to baseline for each sample by dividing each fluorescence value by the minimum fluorescence signal for that sample. Melting curve plots (top) of Cy5 fluorescence (F) versus temperature (T) are transformed into melting peaks (bottom) by plotting –dF/dT vs temperature. Both amplification and genotyping analysis are completed within 45 minutes.

Amplification and genotyping of the C282Y site is illustrated in FIG. 17. The 21-mer fluorescein-probe formed an A:C mismatch with the wild type sequence, lowering the $T_m$ of the probe by 7° C. from the completely complementary duplex. The wild type allele shows no rise in fluorescence above background during amplification since the annealing temperature of the A:C mismatched duplex was below the temperature at which fluorescence was acquired each cycle.

Figure 18:
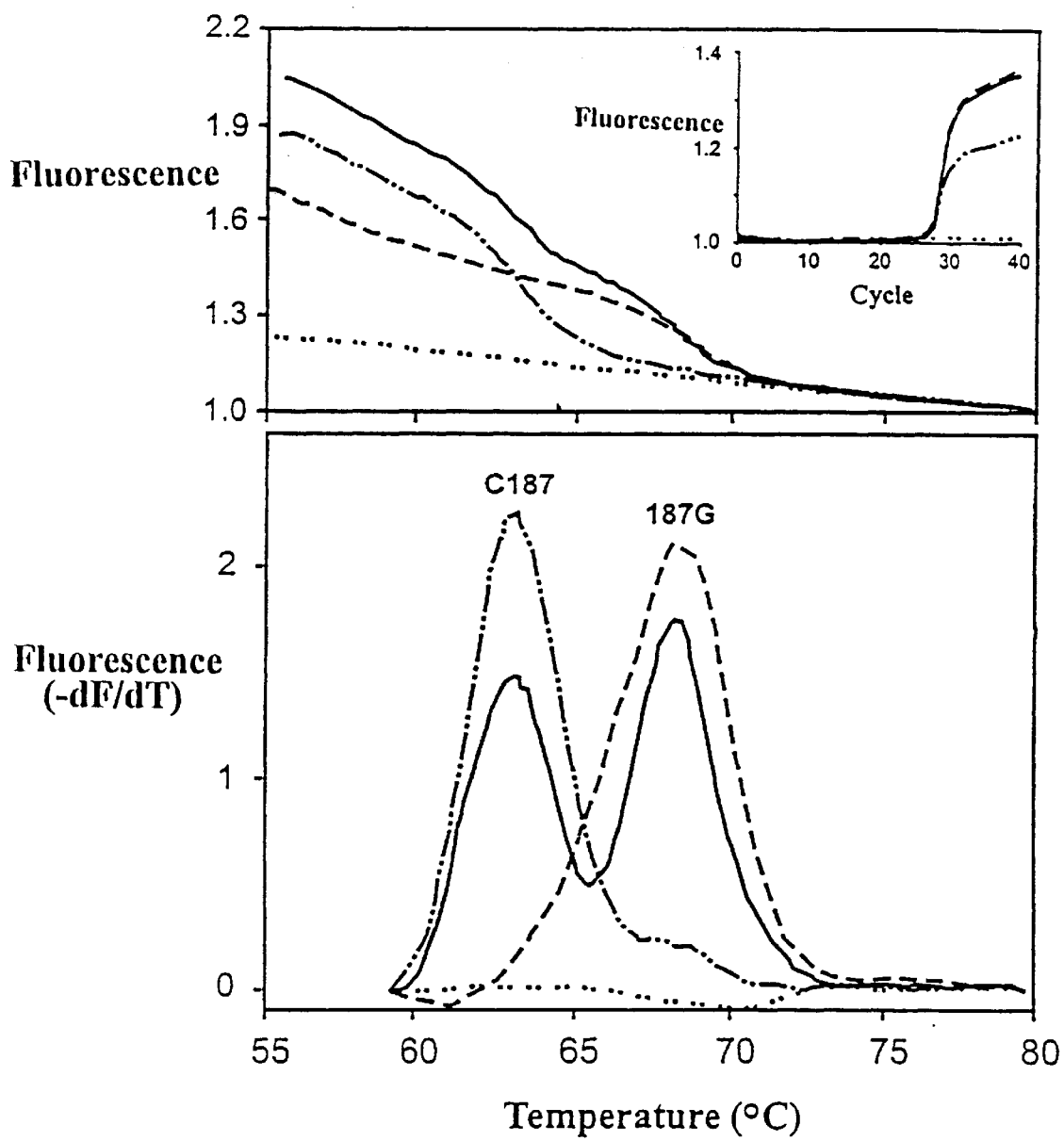
FIG. 18 shows a real-time amplification and genotyping of the H63D site. The inset shows amplification (Cy5 fluorescence vs cycle number) of the 3 genotypes: homozygous wild type (— -- —), heterozygous H63D (—), and homozygous H63D (— — —). A no template control (-- -- --) is also included. Data for amplification and melting curve analysis were normalized to baseline for each sample by dividing each fluorescence value by the minimum fluorescence signal for that sample. Melting curve plots (top) of Cy5 fluorescence (F) versus temperature (T) are transformed into melting peaks (bottom) by plotting –dF/dT vs temperature. Both amplification and genotyping analysis are completed within 45 minutes.

Amplification and genotype analysis for the H63D site is shown in FIG. 18. The G:G mismatch formed at the center of the 27-mer fluorescein-probe created a $\Delta T_M$ of 5.5° C. from the completely Watson-Crick paired duplex. During amplification both the wild type allele and the allele with the H63D mutation were annealed to the probe at the fluorescein acquisition temperature of 62° C.

Figure 19:
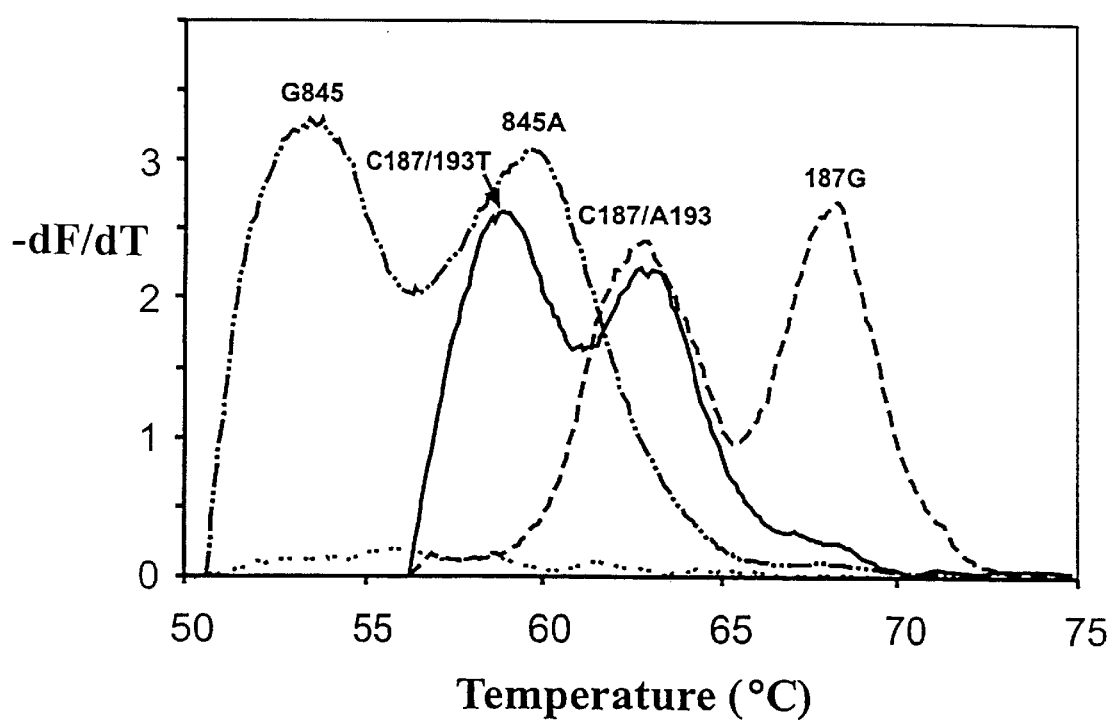
FIG. 19 shows the derivative melting curves of 3 heterozygous genotypes. The 3'-fluorescein labeled probe spanning the region amplified within exon 2 (see FIG. 16) reveals the heterozygous C187G genotype (— — —) at the H63D site and the heterozygous A193T genotype (—) at the S65C site. The probe spanning the C282Y site identifies the heterozygous G845A genotype (— -- —).

Genotyping most samples for the H63D mutation was done with a melting protocol that began at 55° C. to observe melting transitions at 63° C. and 68.5° C. However, 50 samples were analyzed for the H63D mutation with melting curves beginning 10° C. lower at 45° C. Using this melting protocol 4 samples were identified that had a melting peak at 58.5° C., 4.5° C. lower than the melting peak for the wild type allele. Sequencing all 4 samples revealed an A to T transversion at nucleotide 193 of the open reading frame. This transversion is a recently reported polymorphism that results in a serine to cysteine amino acid substitution at codon 65 (S65C). The S65C polymorphism creates an A:A mismatch located 8 base pairs in from the 3'-end of the 27-mer probe (see FIG. 16 and Table 1). When the probe hybridizes to an allele that is wild type at the H63D site but contains the S65C polymorphism, two mismatches are present. This destabilizes the probe by 10° C. compared to the completely complementary duplex. Samples heterozygous at the C282Y, H63D and S65C sites are shown in FIG. 19.

Comparison of genotyping methods

All cases genotyped by adjacent fluorescent hybridization probes agreed with PCR-restriction fragment length analysis. Primers used for analysis of the C282Y site produced a 389 base pair amplicon that was cleaved by SnaBI into fragments of 276 and 113 base pairs in the presence of the C282Y mutation. The PCR product for the H63D site was 241 base pairs long. The H63D mutation destroyed a Bcl I restriction site that upon restriction digestion of the wild type allele yielded fragments of 138 and 103 base pairs. The run time alone required for PCR and genotype analysis by restriction digestion and gel electrophoresis was approximately 3 hours and 30 minutes.

Figure 20:
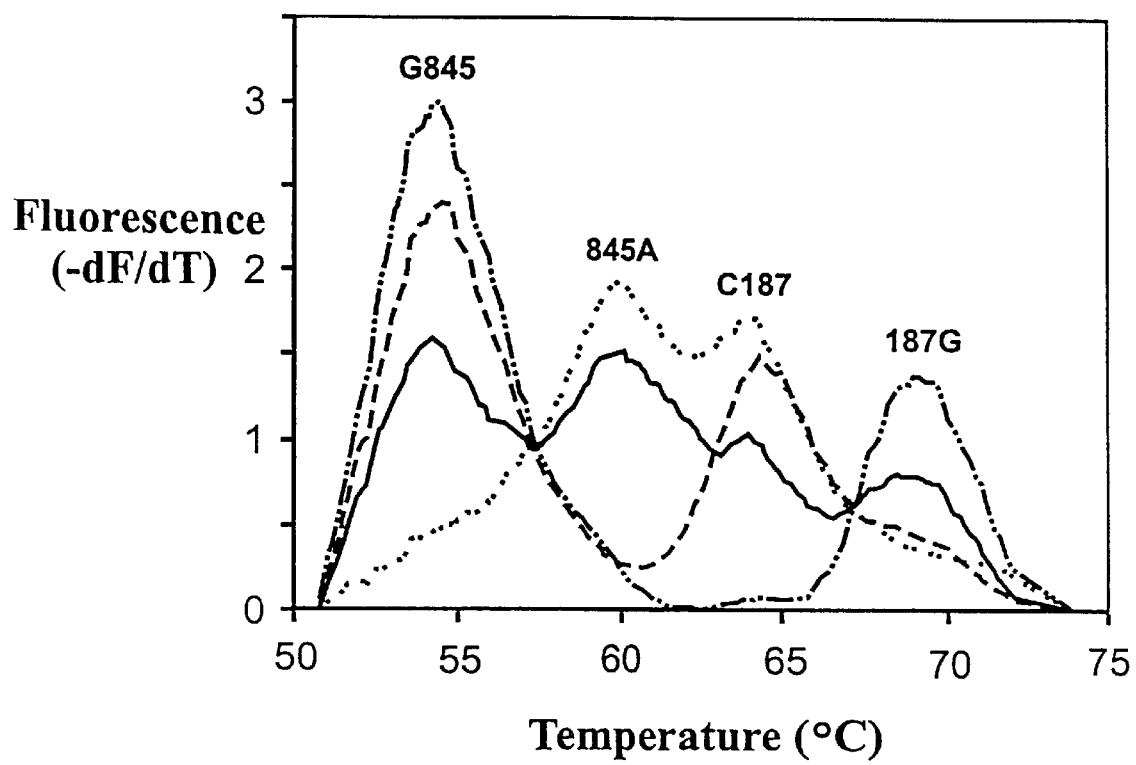
FIG. 20 shows homogenous multiplex genotyping by derivative melting curves for 4 alleles. Shown are 4 samples with different C282Y/H63D genotypes: homozygous C187 (— — —), homozygous G845/homozygous 187G (— -- —), homozygous 845A/homozygous C187 (-- -- --) and heterozygous G845A/heterozygous C187G (—).

In comparison, genotyping with adjacent fluorescent hybridization probes was faster and easier. Amplification and analysis of 24 samples independently at both sites required 45 minutes. No manual manipulation between amplification and genotyping was required. Analysis by multiplexing allowed twice as many samples to be genotyped at both sites in the same amount of time. Genotype analysis by multiplexing with adjacent fluorescent hybridization probes is shown in FIG. 20.

Study of the C282 Y and H63D mutations

One hundred and seventeen patients who met clinical criteria for iron overload and 56 normal controls were selected for analysis of the C282Y and H63D mutations in the HFE gene. Both groups were Caucasian Americans from Utah and neighboring states. The results of this study are summarized in Table 3.

TABLE 3

Analysis of the C282Y and H63D Mutations within the Utah Population

| Genotype* | | Patents with Iron Overload | | Control | |
|---|---|---|---|---|---|
| C282Y | H63D | N | % | N | % |
| hh | HH | 98 | 83.8 | 0 | 0 |
| Hh | HH | 4 | 3.4 | 7 | 12.5 |
| Hh | Hh | 4 | 3.4 | 0 | 0 |
| HH | HH | 6 | 5.1 | 38 | 67.9 |
| HH | Hh | 4 | 3.4 | 10 | 17.9 |
| HH | hh | 1 | 0.9 | 1 | 1.8 |
| Total | | 117 | | 56 | |

| | Allele Frequency (%) | |
|---|---|---|
| C282Y | 204/234 (87.1) | 7/112 (6.3) |
| H63D | 10/234 (4.3) | 12/112 (10.7) |

*hh designates homozygosity for the mutation.
Hh designates heterozygosity.
HH designates homozygous wild type.

Ninety-eight (83.8%) of the patients and none of the controls were homozygous for the C282Y mutation. The C282Y mutation was found in 87% of patient chromosomes and 6.3% of chromosomes from normal controls. The H63D mutation was found in 11% of control chromosomes and only 4.3% of patient chromosomes. There were 8 patients and 7 normal controls heterozygous for the C282Y mutation. One-half of the C282Y heterozygous patients carried the H63D mutation, whereas, there were no compound heterozygous genotypes among the controls.

The S65C polymorphism was found in 4 out of 50 samples. Three of these samples were from the normal control group. The allelic frequency for the S65C variant was 5.5% among the control chromosomes and 2.8% among the patient chromosomes.

Multiplex technology continues to advance both research and routine diagnostics. Sensitive methods of multiplex analysis combined with improved methods of DNA preparation increase the density of information obtained from small amounts of whole blood. This reduces the cost and invasiveness of sample collection and is useful in the analysis of rare samples. Population screening for presymptomatic diagnosis of hereditary hemochromatosis by DNA analysis has been proposed since the first report of the hemochromatosis gene. As of November 1997, the American Medical Association has resolved to establish guidelines for screening for this genetic disease. Given that DNA testing is invariant and there is diverse etiology for elevated blood iron levels, it seems prudent that genetic testing should be included in algorithms for the diagnosis of hemochromatosis. Such large-scale diagnostic tests will become more time efficient and cost-effective through multiplexing.

Hybridization probes can be used to genotype in real-time as shown by the amplification of the C282Y site. When fluorescence is acquired above the $T_m$ for the mismatched probe/allele duplex, only the allele that is completely complementary to the probe shows a change in fluorescence during amplification. Heterozygotes yield half the maximum fluorescence compared to the homozygous perfect match. Advantageously, multiple colors are not necessary for homogenous genotyping with melting curves since multiple alleles can be distinguished with a single probe. Moreover, melting curves prevent false negative results since all alleles are represented and are equally affected by inhibitors within the reaction.

Multiplexing with fluorescent hybridization probes provides rapid and sensitive analysis of multiple alleles. Amplification and genotyping of the HFE gene mutations were performed in approximately 45 min. The HFE assay demonstrated here showed four different alleles differentiated over a 15° C. temperature range.

Adjacent fluorescent hybridization probes are versatile and amenable to multiplexing. The C282Y and H63D mutation sites were co-amplified with different primer sets and simultaneously genotyped by the melting temperatures of multiplexed fluorescent probes. Moreover, the probe spanning the C187G (H63D) mutation could also be used for genotyping the A193T (S65C) polymorphism after the variant was detected by an aberrant melting curve and confirmed by sequencing. The identification of this polymorphism demonstrates genotyping of multiple alleles by a single probe and suggests a potential for fluorescent hybridization probes in scanning for unknown variants.

Summary. From the foregoing discussion, it will be appreciated that continuous fluorescence monitoring during DNA amplification to monitor hybridization is an extraordinarily powerful analytical technique that can be used to detect, simultaneously, mutations at multiple loci. Using the methods described herein and depending on the number of initial template copies present, screening for a specific known mutation or polymorphism can be achieved in five to twenty minutes, more preferably ten to forty five minutes after temperature cycling has begun.

What is claimed is:

1. A method of analyzing a biological sample comprising a nucleic acid sequence for the presence of mutations or polymorphisms at multiple loci of the nucleic acid sequence, said method being conducted in a single reaction vessel and comprising the steps of (a) combining said biological sample with a pair of oligonucleotide PCR primers, a first donor oligonucleotide probe, a first acceptor oligonucleotide probe, a second donor oligonucleotide probe and second acceptor oligonucleotide probe, wherein said pair of oligonucleotide PCR primers is configured for amplifying a selected segment of the nucleic acid sequence; and said first and second donor oligonucleotide probes and said first and second acceptor oligonucleotide probes hybridize to the selected segment so that hybridization of both the first donor oligonucleotide probe and the first acceptor oligonucleotide probe to the selected segment places the first donor oligonucleotide probe and the first acceptor oligonucleotide probe in a resonance energy transfer relationship, and hybridization of both the second donor oligonucleotide probe and the second acceptor oligonucleotide probe to the selected segment places the second donor oligonucleotide probe and the second acceptor oligonucleotide probe in a resonance energy transfer relationship;

(b) adding a thermostable polymerase and amplifying the selected segment of the nucleic acid sequence by the polymerase chain reaction;

(c) illuminating the biological sample and monitoring the fluorescence as a function of temperature.

2. The method of claim 1 further comprising the step of determining the temperature for maximum rate loss of fluorescence from the first acceptor oligonucleotide probe, and determining the temperature for maximum rate loss of fluorescence from the second acceptor oligonucleotide probe.

3. The method of claim 1 wherein the fluorescence of the biological sample as a function of temperature is determined during the polymerase chain reaction.

4. The method of claim 1 wherein the temperature for maximum rate loss of fluorescence from the first acceptor oligonucleotide probe is different than the temperature for maximum rate loss of fluorescence from the second acceptor oligonucleotide probe.

5. The method of claim 4 wherein the first and second donor oligonucleotide probes are each labeled with an identical donor fluorophore and the first and second acceptor oligonucleotide probes are each labeled with an identical acceptor fluorophore.

6. The method of claim 5 wherein the first and second donor oligonucleotide probes are labeled with fluorescein and the first and second acceptor oligonucleotide probes are labeled with Cy5.

7. A kit for analyzing a biological sample comprising a nucleic acid sequence for the presence of mutations or polymorphisms at multiple loci of the nucleic acid sequence, said kit comprising:

a. a mixture of a first donor oligonucleotide probe, a first acceptor oligonucleotide probe, a second donor oligonucleotide probe, and a second acceptor oligonucleotide probe, wherein said first and second donor oligonucleotide probes are each labeled with an identical donor fluorophore and said first and second acceptor oligonucleotides are each labeled with an identical acceptor fluorophore;

said first donor oligonucleotide probe and first acceptor oligonucleotide probe being designed to hybridize to adjacent regions of a first locus of the nucleic acid sequence and said second donor oligonucleotide probe and second acceptor oligonucleotide probe being designed to hybridize to adjacent regions of a second locus of the nucleic acid sequence so that the melting temperature of the set of first donor oligonucleotide probe and first acceptor oligonucleotide probe is different from the melting temperature of the set of second donor oligonucleotide probe and second acceptor oligonucleotide probe;

b. a first pair of oligonucleotide primers configured for amplifying a segment of said nucleic acid sequence that contains the first locus; and c. a thermostable DNA polymerase wherein the probes, primers, and polymerase are provided for use in a single reaction vessel.

8. The kit of claim 7 wherein the first pair of oligonucleotide primers is also configured for amplifying a segment of said nucleic acid sequence that contains the second locus.

9. The kit of claim 7 further comprising a second pair of oligonucleotide primers, wherein the second pair of oligonucleotide primers is configured for amplifying a segment of the nucleic acid sequence that contains the second locus.

10. A method of analyzing a biological sample comprising nucleic acid sequences for the presence of mutations or polymorphisms at multiple loci of the nucleic acid sequences, said method being conducted in a single reaction vessel and comprising the steps of (a) combining said biological sample with a first and second pair of oligonucleotide PCR primers, a first donor oligonucleotide probe, a first acceptor oligonucleotide probe, a second donor oligonucleotide probe and second acceptor oligonucleotide probe, wherein said first pair of oligonucleotide primers is configured for amplifying a first selected segment of said nucleic acid sequences, and said second pair of oligonucleotide primers is configured for amplifying a second selected segment of said nucleic acid sequences; and wherein said first donor oligonucleotide and first acceptor oligonucleotide probes hybridize to the first selected segment and said second donor oligonucleotide and second acceptor oligonucleotide probes hybridize to the second selected segment so that hybridization of both the first donor oligonucleotide probe and the first acceptor oligonucleotide probe to the first selected segment places the first donor oligonucleotide probe and the first acceptor oligonucleotide probe in a resonance energy transfer relationship, and hybridization of both the second donor oligonucleotide probe and the second acceptor oligonucleotide probe to the second selected segment places the second donor oligonucleotide probe and the second acceptor oligonucleotide probe in a resonance energy transfer relationship;

(b) adding a thermostable polymerase and amplifying the first and second selected segments by the polymerase chain reaction;

(c) illuminating the biological sample and monitoring the fluorescence as a function of temperature.

11. The method of claim 10 further comprising the step of determining the temperature for maximum rate loss of fluorescence from the first acceptor oligonucleotide probe, and the determining the temperature for maximum rate loss of fluorescence from the second acceptor oligonucleotide probe.

12. The method of claim 10 wherein the fluorescence of the biological sample as a function of temperature is determined during the polymerase chain reaction.

13. The method of claim 10 wherein the temperature for maximum rate loss of fluorescence from the first acceptor oligonucleotide probe is different than the temperature for maximum rate loss of fluorescence from the second acceptor oligonucleotide probe.

14. The method of claim 13 wherein the first and second donor oligonucleotide probes are each labeled with an identical donor fluorophore and the first and second acceptor oligonucleotide probes are each labeled with an identical acceptor fluorophore.

15. The method of claim 14 wherein the first and second donor oligonucleotide probes are labeled with fluorescein and the first and second acceptor oligonucleotide probes are labeled with Cy5.

16. The method of claim 1 wherein the first and second donor oligonucleotide probes and first and second acceptor oligonucleotide probes are linear and are capable of hybridizing with the nucleic acid sequence during amplification.

17. The method of claim 10 wherein the first and second donor oligonucleotide probes and first and second acceptor oligonucleotide probes are linear and are capable of hybridizing with the nucleic acid sequences during amplification.

18. The method of claim 5 wherein the first and second donor oligonucleotide probes are labeled with fluorescein and the first and second acceptor oligonucleotide probes are labeled with Cy5.5.

19. The method of claim 14 wherein the first and second donor oligonucleotide probes are labeled with fluorescein and the first and second acceptor oligonucleotide probes are labeled with Cy5.5.

20. The kit of claim 7 wherein the thermostable DNA polymerase is native Taq polymerase.

* * * * *